(12) United States Patent
Maiti

(10) Patent No.: US 9,873,732 B2
(45) Date of Patent: Jan. 23, 2018

(54) **POLYCLONAL ANTIBODIES AGAINST *CLOSTRIDIUM DIFFICILE* AND USES THEREOF**

(71) Applicant: IMMUNIMED INC., Winnipeg (CA)

(72) Inventor: Pradip K. Maiti, Winnipeg (CA)

(*) Notice: Subject to any disclaimer, the term of this patent is extended or adjusted under 35 U.S.C. 154(b) by 0 days.

(21) Appl. No.: 14/745,588

(22) Filed: Jun. 22, 2015

(65) Prior Publication Data

US 2015/0368320 A1 Dec. 24, 2015

Related U.S. Application Data

(60) Provisional application No. 62/015,339, filed on Jun. 20, 2014.

(51) Int. Cl.

| | | |
|---|---|---|
| *C07K 16/02* | (2006.01) | |
| *A61K 39/08* | (2006.01) | |
| *C07K 16/12* | (2006.01) | |
| *A61K 39/395* | (2006.01) | |
| *A61K 39/00* | (2006.01) | |

(52) U.S. Cl.
CPC .............. *C07K 16/02* (2013.01); *A61K 39/08* (2013.01); *A61K 39/39591* (2013.01); *C07K 16/1282* (2013.01); *A61K 2039/505* (2013.01); *C07K 2317/11* (2013.01); *C07K 2317/23* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 6,969,520 B2 * | 11/2005 | Thomas, Jr. | ............ | C07K 14/33 424/167.1 |
| 8,257,709 B2 | 9/2012 | Ambrosino et al. | | |
| 8,921,529 B2 * | 12/2014 | Shone | ................ | C07K 16/1282 424/167.1 |
| 8,986,697 B2 | 3/2015 | Ma | | |
| 9,139,625 B2 * | 9/2015 | Cutting | .................. | C07K 14/33 |
| 2007/0071795 A1 | 3/2007 | Pradip et al. | | |
| 2012/0276059 A1 * | 11/2012 | Boone | ............. | G01N 33/56911 424/93.4 |
| 2013/0004561 A1 * | 1/2013 | Shone | ................ | C07K 16/1282 424/450 |
| 2015/0017181 A1 * | 1/2015 | Kelly | .................... | A61K 38/14 424/150.1 |
| 2015/0368320 A1 * | 12/2015 | Maiti | ..................... | A61K 39/08 424/158.1 |
| 2016/0083457 A1 * | 3/2016 | Lyras | ................ | C07K 16/1282 424/157.1 |

FOREIGN PATENT DOCUMENTS

| | | |
|---|---|---|
| CA | 2560283 | 3/2007 |
| WO | 9413264 | 6/1994 |
| WO | 9902188 | 1/1999 |
| WO | 2014169344 | 10/2014 |

OTHER PUBLICATIONS

Babcock et al, Infection and Immunity, Nov. 2006, 74/11:6339-6347.*
Giannasca et al, Infection and Immunity, Feb. 1999, 67/2:527-538.*
Leav et al, Vaccine, 2010, 28:965-969.*
Ward et al, Infection and Immunity, Oct. 1999, 67/10:5124-5132.*
Lowy et al, New England Journal of Medicine, Jan. 21, 2010, 362/3:197-205.*
Aslam et al, Lancet Infect. Dis., 2005, 5:549-557.*
Ghose, Emerging Microbes and Infections, 2013, 2:e62, 8 pages.*
Kink et al, Infection and Immunity, May 1998, 66/5:2018-2025.*
Giannasca et al, Vaccine, 2004, 22:848-856.*
Hussack et al, Clinical and Experimental Gastroenterology, 2016, 9:209-224.*
Stoddart et al, Current Opinion in Infectious Disease, 2002, 15:513-518.*
Ghose et al, Infection and Immunity, Jun. 2007, 75/6:2826-2832.*
Leuzzi et al, Infection and Immunity, Aug. 2013, 81/8:2851-2860.*
Lyras et al, Nature, Apr. 30, 2009, 458:1176-1181.*
Humphreys et al, Clinical and Vaccine Immunology, Jul. 2014, 21/7:913-923.*
Mizrahi et al, Anaerobe, 2014, 30:210-219.*
Mulvey et al, Journal of Medical Microbiology, 2011, 60:1181-1187.*
Simon et al, Antibodies, 2014, 3:272-288.*
Permpoonpattana et al, Infection and Immunity, Jun. 2011, 79/6:2295-2302.*
Kink J A et al: "Antibodies to Recombinant Clostridium Difficile Toxins A and B are Effective Treatment and Prevent Relapse of C. Difficile-Associated Disease in a Hamster Model of Infection", Infection and Immunity, American Society for Microbiology, US, vol. 66, No. 5, May 1, 1998, pp. 2018-2025, ISSN: 0019-9567.
Min S Song et al: "Growth Inhibition of Clostridium Perfringens Vegetative Cells and Spores using Chicken Immunoglobulin Y", Journal of Food Safety 2009 Correspondence Address, Hoon H. Sunwood, CJ Foods R&D, CJ Coporation 636, Guro-Dong, Guro-Gu, Seoul, South Korea., vol. 29, No. 4, Jan. 1, 2009, pp. 211-250.

* cited by examiner

*Primary Examiner* — Nita M. Minnifield
(74) *Attorney, Agent, or Firm* — Michael R. Williams; Ryan W. Dupuis; Ade & Company Inc.

(57) ABSTRACT

A polyclonal antibody composition prepared from eggs of immunized hens is used to treat *C. difficile* infections. Respective groups of hens are immunized with Toxin A or Toxin B of *Clostridium difficile* or a *Clostridium difficile* spore preparation. The polyclonal antibodies are recovered from eggs pooled from the immunized hens and the resulting powder is administered in a therapeutically effective amount to individuals infected with or suspected of being infected with *C. difficile*.

18 Claims, 10 Drawing Sheets

POLYCLONAL ANTIBODIES AGAINST *CLOSTRIDIUM DIFFICILE* AND USES THEREOF

PRIOR APPLICATION INFORMATION

The instant application claims the benefit of U.S. Provisional Patent Application Ser. No. 62/015,339, filed Jun. 20, 2014, entitled "Antibodies against *Clostridium difficile* and uses thereof", the contents of which are incorporated herein by reference.

FIELD OF THE INVENTION

The invention relates generally to the field of compositions for the treatment of *Clostridium difficile* infections and *Clostridium difficile* associated diseases. More specifically, the invention relates to a polyclonal antibody composition prepared from eggs of immunized hens. Yet more specifically, the invention relates to a polyclonal antibody composition prepared from eggs of hens immunized with Toxin A and Toxin B of *Clostridium difficile* and a *Clostridium difficile* spore preparation that is administered orally to patients for example humans to treat *Clostridium difficile* infections and the symptoms associated therewith.

BACKGROUND OF THE INVENTION

*Clostridium difficile* (*C. difficile* or *C. diff*) is a Gram-positive, spore-forming bacterium that causes hospital-acquired as well as community-acquired enteric infections. Infections can be asymptomatic but generally lead to *C. diff*-associated diarrhea, pseudomembranous colitis, colitis and death (Halsey, J:, 2008, Am. J. Health Syst. Pharm. 65: 705-715; Lessa, F. C. et al., 2012, Clin. Infect. Dis. 55: S65-70). Approximately 20% of individuals who are hospitalized become colonized with *C. difficile* during hospitalization, and more than 30% of these patients develop diarrhea. Thus, *Clostridium difficile* infection (CDI) or *Clostridium difficile*-associated disease (CDAD) is now a major problem in hospitals worldwide (Kutty, P. K., et al., 2010, Emerg. Infect. Dis 16: 197-204; O'Brien, J. A. et al, 2007, Infect. Cont. & Hosp. Epidemiology 28: 1219-1227.

The rate of CDI is steadily increasing both in North America and Europe (Goorhuis, A et al., 2008, J. Clin Microb. 46: 1157-1158; Gravel, D. et al., 2009, Clin. Infect. Dis. 48: 568-576). It is estimated that 1.1 to 3 million patients are infected with *C. diff* and there are 30,000 *C. diff*-related deaths each year in the US alone3. Similar numbers of people are affected with CDI in Europe, costing the EU health care an estimated $4.4 billion each year (Lessa, F. C. et al., 2015, N. Engl. J. Med. 372: 825-834).

CDI has surpassed methicillin-resistant *staphylococcus aureus* (MRSA) as the most frequent infections acquired in the hospital and controlling CDI has proven to be a challenge (Miller, B A. et al., 2011, Infect. Control Hosp. Epidemiol 32: 387-390). In the U.S., patients with *C. diff* are hospitalized for an extra 3.6-7 days, costing more than $8.2 billion (Lessa, F. C. et al 2015) (6; 7; 8.

*C. difficile* infection is often but not always induced by antibiotic disruption of the colonic flora through the use of antibiotics such as clindamycin, cephalosporins, and fluoroquinolones. This perturbation in the colonic microenvironment, along with exposure to *C. difficile* spores, leads to mucosal *C. difficile* colonization. This colonization may result from the presence of a pre-existing antibiotic resistant *C. difficile* or concomitant exposure to *C. difficile* spores, particularly in hospitals. Approximately one-third of all patients that become colonized develop CDAD, which can result in severe diarrhea, perforation of the colon, colectomy and death. CDAD results from the acquisition and proliferation of *C. difficile* in the gut, where *C. difficile* bacteria produce toxin A and toxin B, two important virulence factors of CDAD. Toxins A and B of *C. difficile* show considerable sequence and structural homology. Both have a C-terminal receptor-binding domain containing multiple repeating sequences, a central hydrophobic domain and an N-terminal glucosyltransferase domain. The receptor-binding domain mediates binding of the toxins to intestinal epithelial cells via host receptors that remain poorly defined in humans. Following internalization via an endosomal pathway, the central hydrophobic domain inserts into the membrane of the endosome. The acidic pH of the endosome triggers pore formation and translocation of the amino-terminal domains of the toxins into the cytosol. Glucosylation of the cytosolic target Rho GTPases leads to disruption of the cytoskeleton and cell death. Toxins A and B demonstrate different pathological profiles and have potential synergy in causing disease.

Current treatment for *C. difficile* infection (CDI) is the use of certain antibiotics, such as for example but by no means limited to Metronidazole, Vancomycin, and Fidaxomycin, either alone or in combination. However, efficacies of these antibiotics are limited by incomplete response rates with increasing re-infection and recurrence rates[2]. The antibiotic therapy does not provide complete protection to all patients; as a result, 25-40% of patients suffer from *C. difficile* recurrent infections (Figueroa, I. et al., 2012, Clin. Infect. Dis. 55: S104-S109).

The risk of recurrence is increased in patients who have already had one recurrence, rising from 20% after an initial episode to more than 60% in patients with a history of previous *C. difficile* infection. Furthermore, *C. difficile* strains are becoming resistant to antibiotic therapies. As a result, cure rates are decreasing and the rate of recurring infections is increasing along with increased severity and mortality even with antibiotic therapy (Kelly, C. P. and Lamont, J. T., 2008, N. Engl. J. Med. 359: 1932-1940; Goorhuis, A et al 2008; Gravel, D. et al 2009).

The prevalence of *C. difficile* infection has been increasing steadily, particularly in the elderly, who are often frail. Approximately one-third of patients with a *C. difficile* infection have recurrences of their infection, usually within two months of the initial illness. Repeat infections tend to be more severe than the original disease. Older adults and people with weakened immune systems are particularly susceptible to recurring infections (Kee, V. R., 2012, Am. J. Geriatric Pharm. 10: 14-24). If not treated promptly and appropriately, the complications of *C. difficile* infection include dehydration, kidney failure, bowel perforation, toxic megacolon, which can lead to rupture of the colon, and death. *C. difficile* has become the most common cause of health-care associated infections in US hospitals. Health-care cost related to *C. difficile* infections are estimated to be as much as $4.8 billion for acute care facilities alone. In addition, *C. difficile* infection has been increasing reported outside the acute care facilities, including in community and nursing home settings, where infection can be treated without hospitalization. The elderly people who are at the high risk of getting *C. difficile* infection have other debilitating diseases like cancer, HIV, undergoing surgery, prolonged treatments with antibiotics, other gastrointestinal diseases.

The incidence and severity of CDI have increased significantly due in part to the emergence of unusually virulent, antibiotic resistant strains. Chief amongst these are strains characterized as group BI by restriction endonuclease analysis, North American pulse-field type 1 (NAP1) by pulse-field gel electrophoresis and ribotype 027 by polymerase chain reaction. These hyper-virulent strains are often also toxin-hyperproducers. For example, isolates of ribotype 027 produced higher levels of toxin and exhibited slower growth compared to other isolates (Figueroa, I. et al 2012).

These strains cause CDI with a directly attributable mortality more than 3 fold that observed previously.

Furthermore, isolates demonstrating increased spore production appear to be linked to more severe *C. difficile* infections (Merrigan, M. et al., 2010, J. Bacteriol. 192: 4904-4911; Carlson, P. E. et al., 2013, Anaerobe 24: 109-116).

Consequently, there is a need for more effective treatments that target the life-threatening diseases caused by *C. difficile*, and, in particular, the potent toxins that are produced by *C. difficile*, for prophylactic and therapeutic benefit. There is an unmet medical need for successful and lasting treatments for *C. difficile*-associated disease that offer lower potential for developing resistance and higher potential for successful patient response and disease resolution, leading to disease eradication.

Thus, it is clear that the disease/infection caused by *C. difficile* puts the lives of people of all ages in jeopardy, both in nosocomial settings and in the community at large. In today's world, there is an ever present risk of *C. difficile* infection for those who face hospitalization or who are in long-term care. New therapeutics are therefore urgently needed since efficacy of the current antibiotics appears to be decreasing. Consequently, there is a clear unmet medical need for an effective novel non-antibiotic therapy that targets the life-threatening disease caused by the "super bug", *C. difficile*. The present invention meets this need and provides compositions and methods for safe, effective treatment and prevention of CDI or CDAD.

Immune approaches attempted so far include vaccination (Salcedo, J. et al., 1997, Gut. 41: 366-370), the use of anti-*Clostridium difficile* colostral or whey protein from cows immunized with *C. difficile* and passive immunization with intravenous immunoglobulin (IVIg) (Surawicz & Alexander, 2011, Nature Rev. Gastro. Hep. 8: 339-339), Despite some encouraging studies in a limited number of patients, neither specific cow antibodies nor polyclonal IVIg has become a commonly used treatment.

Vaccination offers the potential advantage of generating a polyclonal response, but the disadvantages relate to the timing of vaccine administration relative to the perceived risk of infection and variability in the patient's immune response.

Furthermore, the manufacture of colostrum or serum polyclonal antibodies from cow, sheep, alpaca or other species for therapeutic use can have production quality difficulties in controlling the variability of batch-to-batch antitoxin activities (titer and specificity). In addition, total production capacity of methods such as these have limits and there can be immunogenicity concerns.

U.S. Pat. No. 8,986,697 teaches monoclonal antibodies which bind to toxin A and toxin B of *C. difficile.*

U.S. Pat. No. 8,257,709 also teaches monoclonal antibodies which bind to toxin A and toxin B of *C. difficile.*

U.S. Pat. No. 8,921,529 teaches ovine antibodies raised against *C. difficile* toxin A, Toxin B and/or binary toxin which are administered as sheep serum.

Polyclonal antibodies comprise a large number of antibodies with different specificities and epitope affinities. For production purposes these antibodies are generally purified from the serum of immunised animals were the antigen of interest stimulates the B-lymphocytes to produce a diverse range of immunoglobulin's specific to that antigen.

Monoclonal antibodies represent a single B lymphocyte generating antibodies to one specific epitope.

Polyclonal antibodies are poly-specific in that a polyclonal antibody preparation is composed of many different antibodies, each recognising a distinct epitopes of one antigen. While in some uses, such as simple detection of a specific antigen, the fact that a polyclonal antibody preparation will bind to more than one epitope on a specific antigen is not an issue, this is generally considered to be a negative in therapeutic uses as many of the polyclonal antibodies are likely to recognize non-neutralizing epitopes and therefore may be of limited value from a therapeutic standpoint. Cross-reactivity can also be a concern.

Monoclonal antibodies are produced from an immortal cell line and therefore it is possible to produce unlimited quantities of highly specific antibodies. Furthermore, all batches will be identical and specific to just one epitope, which is generally considered to be a particular advantage for therapeutic treatments.

However, neutralizing monoclonal antibodies with high affinities, in vitro potencies or very high levels of protection against infection in most animal models can be very difficult to obtain.

Furthermore, many monoclonal antibodies which show successful treatment of a given disease in lower mammals have failed when used on higher primates for reasons that cannot always be explained.

Furthermore, polyclonal antibodies have a significant advantage in that they are less sensitive to antigen changes than monoclonal antibodies. As such, polyclonal antibodies are more tolerant to mutations and/or effective against different strains and/or isolates, by virtue of recognizing multiple epitopes. Specifically, polyclonal antibodies recognize multiple inhibitory epitopes on a single target and accordingly can achieve beyond what is possible against a single monoclonal antibody.

For example, while monoclonal antibodies against the cell wall binding domains of the *C. difficile* toxin proteins have demonstrated neutralizing capabilities, their activity in cell-based assays is significantly weaker than that observed for polyclonal antibody mixtures (Corthier, G. et al., 1991, Infect. Immun. 59: 1192-1195; D. F. M. Thomas et al., 1982, The Lancet, Jan. 9, 1982, pp 78-79; Lyerly, D. M. et al., 1985,J. Clin. Micro. 21: 12-14).

Clearly, a therapeutic composition for treating *C. difficile* infections and *C. difficile* associated diseases which has broad applicability, particularly against hypervirulent strains, that can be easily and reproducibly produced and will be well tolerated by patients suffering from CDAD is needed.

SUMMARY OF THE INVENTION

The present invention provides compositions and methods for the treatment and prevention of gastro-enteric infections including CDI and other infections in human and other animals.

In one aspect, the invention provides compositions comprising antibodies developed against and/or targeting *C. difficile* virulent antigens.

In some embodiments, the antibodies target *C. difficile* toxins A, toxin B, spores and/or other virulent antigens responsible for the pathogenesis of CDI. In some embodiments, the antibodies target *C. difficile* toxin A, toxin B, or binary toxin. In some embodiments, the antibodies target *C. difficile* spores. In some embodiments, the antibodies target other virulent antigens responsible for the pathogenesis of CDI.

In some embodiments, the antibodies are polyclonal antibodies. In some embodiments, the polyclonal antibody preparation is referred to as IMM-001.

In some other embodiments, the invention provides compositions comprising antibodies targeting other gastro-enteric infections such as Irritable Bowel Syndrome (IBS) and methane Gas production.

In some embodiments, the polyclonal antibodies are generated by immunizing animals, for example, birds with the pathogen of interest. In some embodiments, the polyclonal antibodies are generated by immunizing animals with a virulent antigen of the pathogen. In some other embodiments, the polyclonal antibodies are generated by immunizing animals with an inactivated or attenuated strain of the pathogen. In some embodiments, the polyclonal antibodies are produced in the form of eggs from the birds. In some embodiments, the polyclonal antibodies are purified, recovered or isolated from the eggs. In some embodiment, the immunized birds are chickens or hens.

In some embodiments, the polyclonal antibodies are used in the preparation of a composition suitable for oral consumption.

In some embodiments, the polyclonal antibodies are used in the preparation of a pharmaceutical composition for the treatment of a confirmed or suspected *C. difficile* infection.

In one aspect, the invention provides egg-derived pathogen-specific polyclonal antibody therapeutics.

In another aspect, the invention provides a method of treating a subject suspected of having or diagnosed with a *C. difficile* infection, the method comprising administering to the subject an effective amount of the compositions or the polyclonal antibodies described herein.

In another aspect, the invention provides a method of preventing a subject from developing CDI or CDAD, the method comprising administering to the subject the compositions or the antibodies described herein. For example, the subject may be an individual who is known or suspected of having a *C. difficile* infection or who is known or suspected of or at risk of having come into contact with *C. difficile* or *C. difficile* spores.

In some embodiments, the subject is a human. In other embodiments, the subject is a non-human animal.

In some embodiments, the method comprises administering the composition or the polyclonal antibodies to the subject orally.

In one aspect, the invention provides a method for generating the antibodies of the invention. In some embodiments, the method comprises immunizing animals for example birds with the pathogen of interest, a virulent antigen of the pathogen, or an inactivated or attenuated strain of the pathogen. In some embodiments, the method further comprises harvesting eggs from the birds. In some embodiments, the method further comprises purifying the antibodies from the eggs. In some embodiment, the immunized birds are chickens or hens.

According to a first aspect of the invention, there is provided a method of preparing a polyclonal antibody composition for treating or preventing or prophylactically treating a *Clostridium difficile* associated disease comprising:

a) inoculating a first group of egg-laying hens with an antigen prepared from *Clostridium difficile* Toxin A;

b) inoculating a second group of egg-laying hens with an antigen prepared from *Clostridium difficile* Toxin B;

c) inoculating a third group of egg-laying hens with an antigen prepared from *Clostridium difficile* spores;

d) collecting eggs laid by said first group, said second group and said third group; and e) recovering polyclonal antibodies from said collected eggs.

The antigens may be administered to the hens in combination with an adjuvant. In some embodiments the adjuvant is Montanide-ISA-70.

In some embodiments, the polyclonal antibodies are recovered from the collected eggs by freeze-drying the eggs or by spray-drying.

Preferably, the polyclonal antibody composition has a reciprocal titer of <128,000.

According to another aspect of the invention, there is provided the use of the polyclonal antibody composition described above to treat or prevent or prophylactically treat a *Clostridium difficile* infection and/or a *Clostridium difficile* associated disease, as discussed herein.

In one aspect of the invention, there is provided a method for treating or preventing or prophylactically treating a *Clostridium difficile* associated disease comprising administering to an individual in need of such treatment an effective amount of a polyclonal antibody composition, said polyclonal antibody composition being prepared by a method comprising:

a) inoculating a first group of egg-laying hens with an antigen prepared from *Clostridium difficile* Toxin A;

b) inoculating a second group of egg-laying hens with an antigen prepared from *Clostridium difficile* Toxin B;

c) inoculating a third group of egg-laying hens with an antigen prepared from *Clostridium difficile* spores;

d) collecting eggs laid by said first group, said second group and said third group;

e) recovering polyclonal antibodies from said collected eggs; and f) administering an effective amount of the polyclonal antibodies to an individual in need of such treatment.

In another aspect of the invention, there is provided a polyclonal antibody composition for treating or preventing or prophylactically treating a *Clostridium difficile* associated disease characterized in that said polyclonal antibody composition being prepared by a method comprising:

a) inoculating a first group of egg-laying hens with an antigen prepared from *Clostridium difficile* Toxin A;

b) inoculating a second group of egg-laying hens with an antigen prepared from *Clostridium difficile* Toxin B;

c) inoculating a third group of egg-laying hens with an antigen prepared from *Clostridium difficile* spores;

d) collecting eggs laid by said first group, said second group and said third group; and e) recovering polyclonal antibodies from said collected eggs.

According to a further aspect of the invention, there is provided use of a polyclonal antibody composition for treating or preventing or prophylactically treating a *Clostridium difficile* infection characterized in that said polyclonal antibody composition is prepared by a method comprising:

a) inoculating a first group of egg-laying hens with an antigen prepared from *Clostridium difficile* Toxin A;

b) inoculating a second group of egg-laying hens with an antigen prepared from *Clostridium difficile* Toxin B;

c) inoculating a third group of egg-laying hens with an antigen prepared from *Clostridium difficile* spores;

d) collecting eggs laid by said first group, said second group and said third group; and e) recovering polyclonal antibodies from said collected eggs.

IMM-001 polyclonal antibodies showed strong reactivity against toxins produced by all seven clinical isolates of *C. difficile* with four different ribotype, 002, 003, 019 and 027. However, the reactivity was strongest with 1/10 dilution and weakest with the 1/500 dilution of culture supernatant. The Figure demonstrates that clinical isolates of *C. difficile* produced variable amounts of toxins in vitro in the culture supernatants. IMM-001 antibodies exhibited strong reactivity and the reactivity determined to be toxin-concentration dependent.

Figure 3:
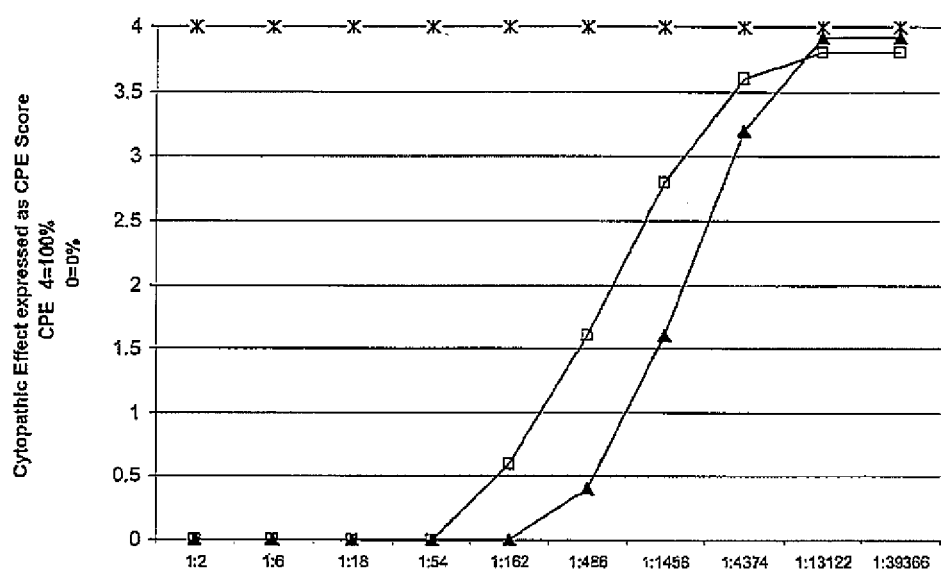

FIG. 3. IMM-001 Neutralizing cytopathic effect of *C. difficile* Toxin A and Toxin B mediated cytotoxicity using cell-based assay with IMR-90 cells in vitro. Well established, IMR-90, Human lung fibroblast cell line, were incubated with *C. difficile* toxin A+toxin B in different concentrations. Cytopathic effects (CPE) were determined by visual inspection of rounded cells under microscope. A CPE score 4,=100% cell cytotoxicity, and CPE score 0=0% cytotoxicity or 100% neutralization. Results shown in figure that IMM-001 polyclonal antibodies are able to neutralize 100% cytotoxicity-mediated by toxin A and toxin B in IMM-001 antibody dose-dependent manner, IMM-001 showed toxin neutralization at 1:162 dilutions, when Goat polyclonal antibodies used as positive control showed neutralization at 1:54 dilution.

Figure 4:
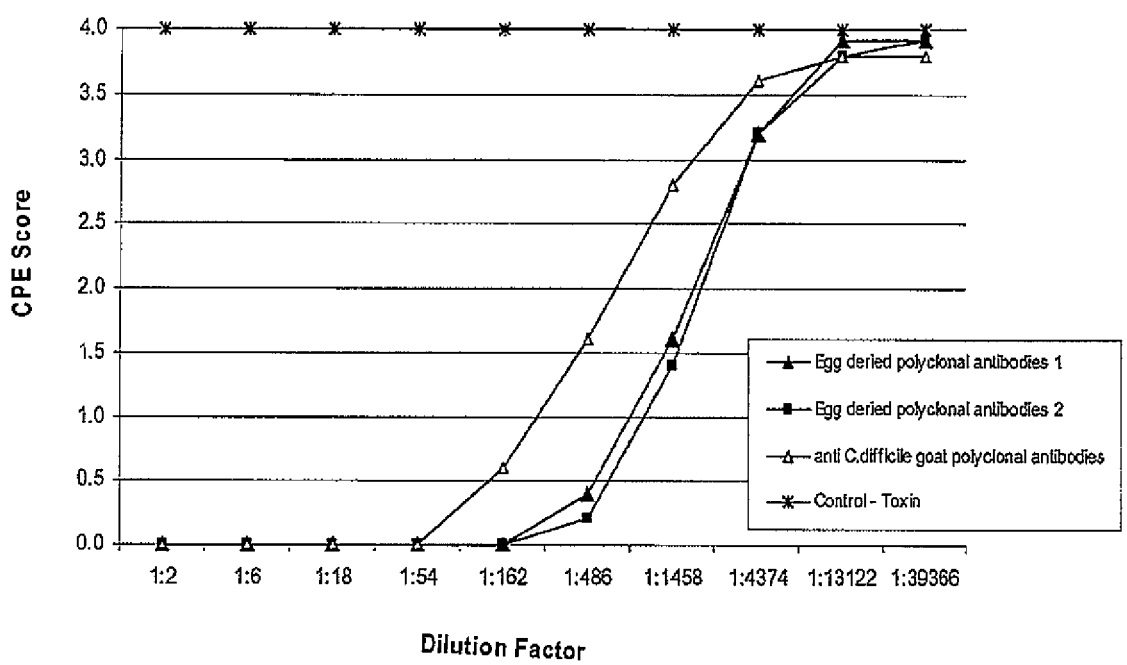

FIG. 4. Neutralization of *C. difficile* Toxin A and B cytotoxicity in IMR-90 cells by Goat polyclonal antibodies and Egg-derived polyclonal antibodies IMM-001.

The cytopathic effects were determined by observing the percent of cells that had become rounded in presence of toxins. When there is no cytopathic effect, i.e. cells that had not become rounded with toxin in presence of antibodies, toxin was considered neutralized. IMM-001 showed toxin neutralization at 1:162 dilutions, when Goat polyclonal antibodies used as positive control showed neutralization at 1:54 dilution.

Figure 5:
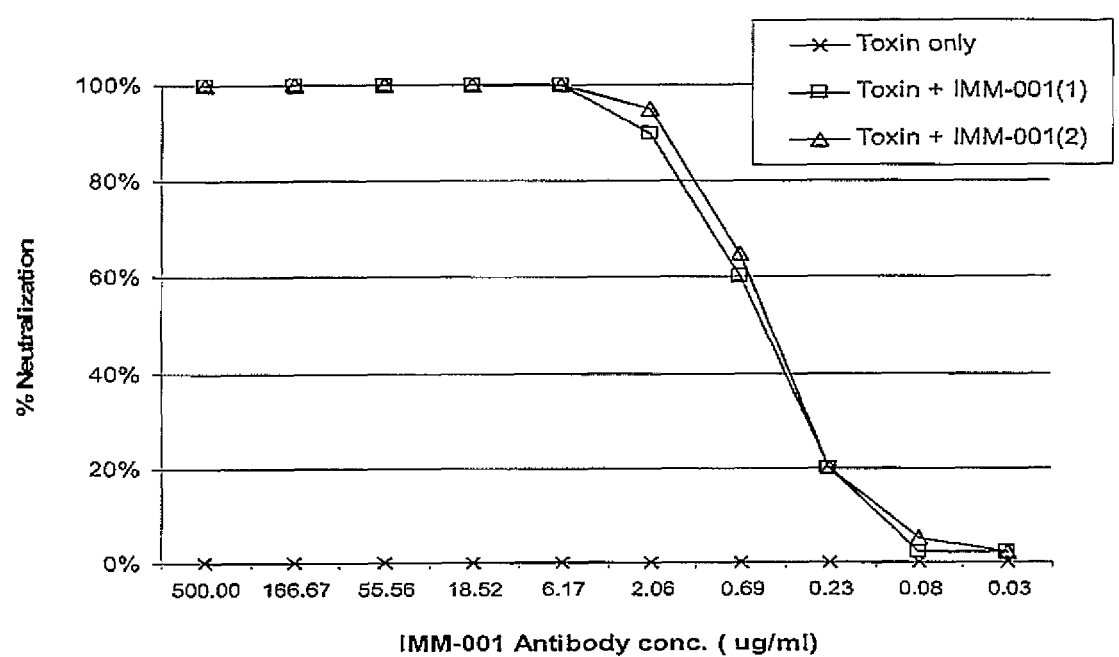

FIG. 5. Toxin neutralization ability of IMM-001 polyclonal antibodies in vitro. No toxin neutralization activity was detected when the cells were incubated with toxin alone. In contrast, maximum neutralization activity (100%) was achieved when the toxin was mixed with IMM-001 antibody concentration at 6.17 µg/mL or higher. However, the toxin neutralization ability was diminished to zero when the lowest amount (0.06 µg/mL) of IMM-001 antibodies was added to the toxin.

Figure demonstrated that IMM-001 polyclonal antibodies are capable of neutralizing cytopathic effects of *C. difficile* toxins on IMR-90 cells in vitro and the efficacy is IMM-001 polyclonal antibody concentration-dependent.

Figure 6:
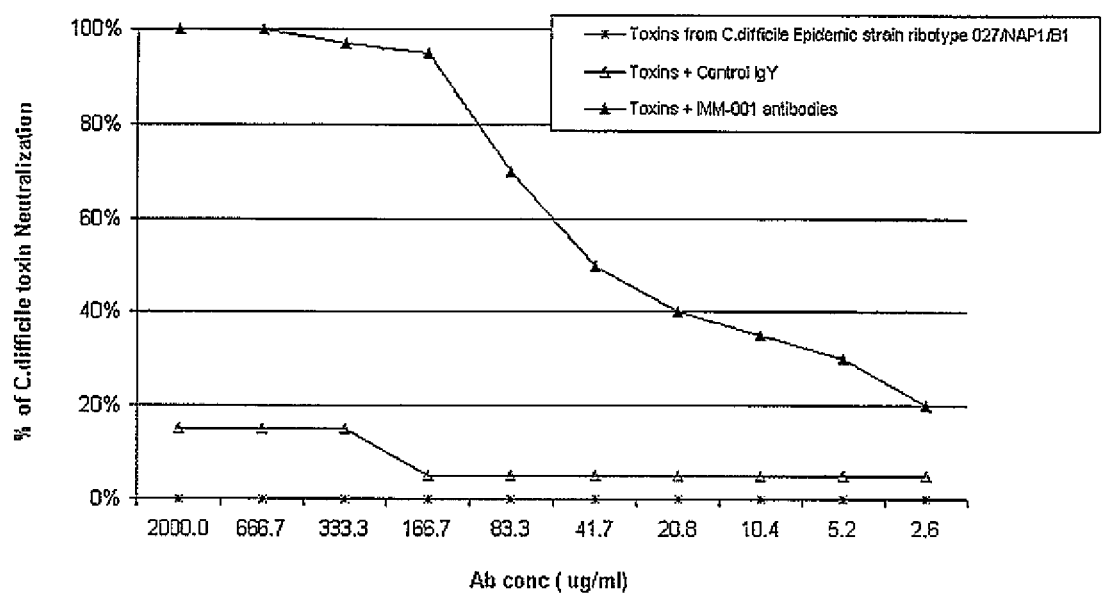

FIG. 6. Toxin neutralization ability of IMM-001 to toxins produced by hypervirulent *C. difficile* strain in cell-based assay using T-84 cells.

The Figure demonstrates that toxin A & B alone demonstrated 100% cytopathic effect with no toxin neutralization on T-84 cells. *C. difficile* toxin+control egg powder showed 85-90% cytopathic effect with 10-15% toxin neutralization on T-84 cells. In contrast, toxin A & B+IMM-001 antibody showed 0% cytopathic effect with 100% toxin neutralization, but the toxin neutralization ability of IMM-001 antibody is determined to be antibody dose-dependent.

Figure 7:
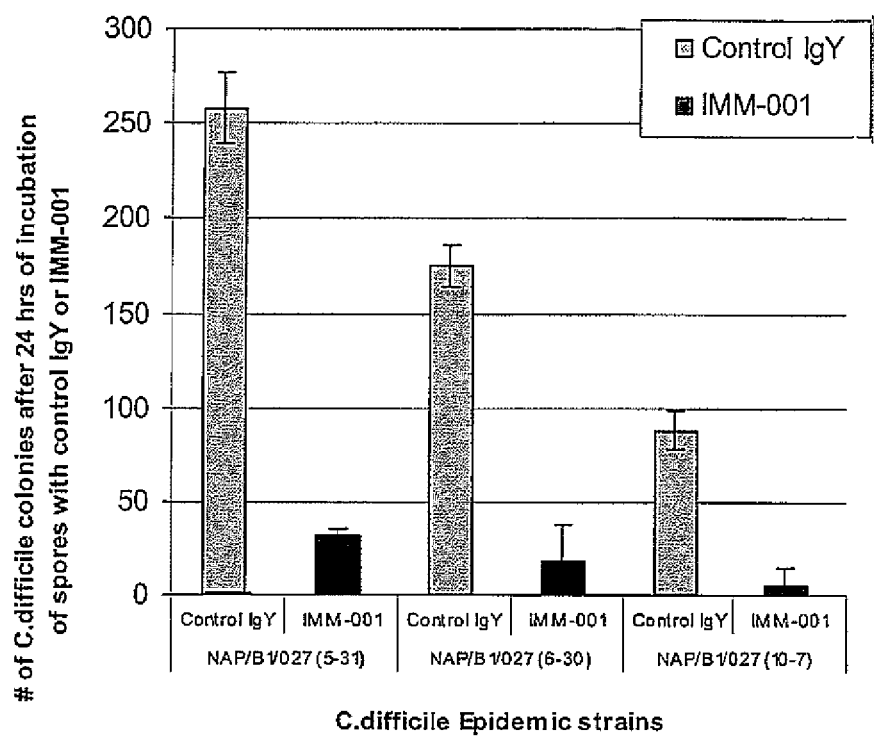

FIG. 7. Effect of IMM-001 antibodies on growth inhibition of hypervirulent *C. difficile* strains. As shown in the Figure, that the 90-260 colonies were detected after incubation of a fixed number of *C. difficile* spores with control egg powder from un-vaccinated chicken. In contrast, only 5-20 colonies were detected following incubation of the same number of spores of *C. difficile* hypervirulent strains with IMM-001 antibodies.

Figure 8:
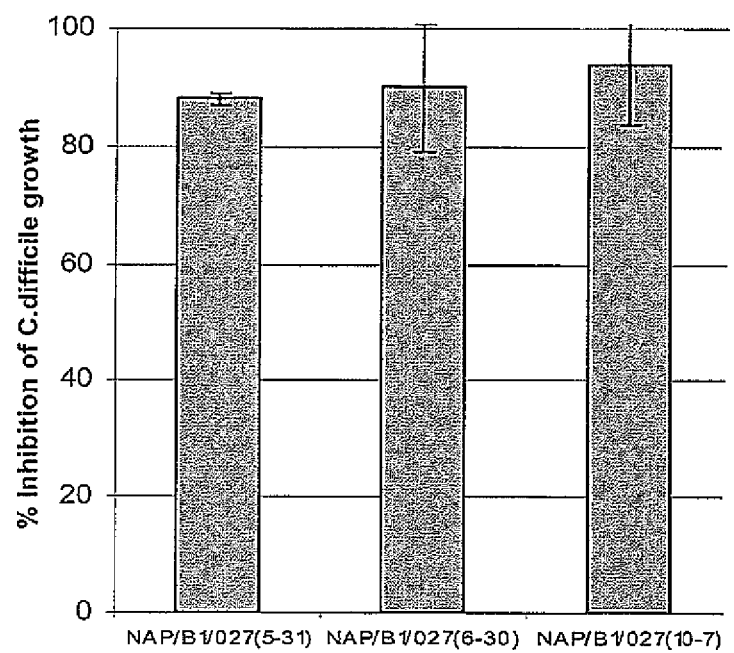

FIG. 8. Effect of IMM-001 antibodies in vitro on inhibition of growth of hypervirulent *C. difficile* strains.

The Figure demonstrated that IMM-001 antibodies inhibited >80% growth of all three *C. difficile* isolates of hypervirulent NAP/B1/027 strains.

Figure 9:
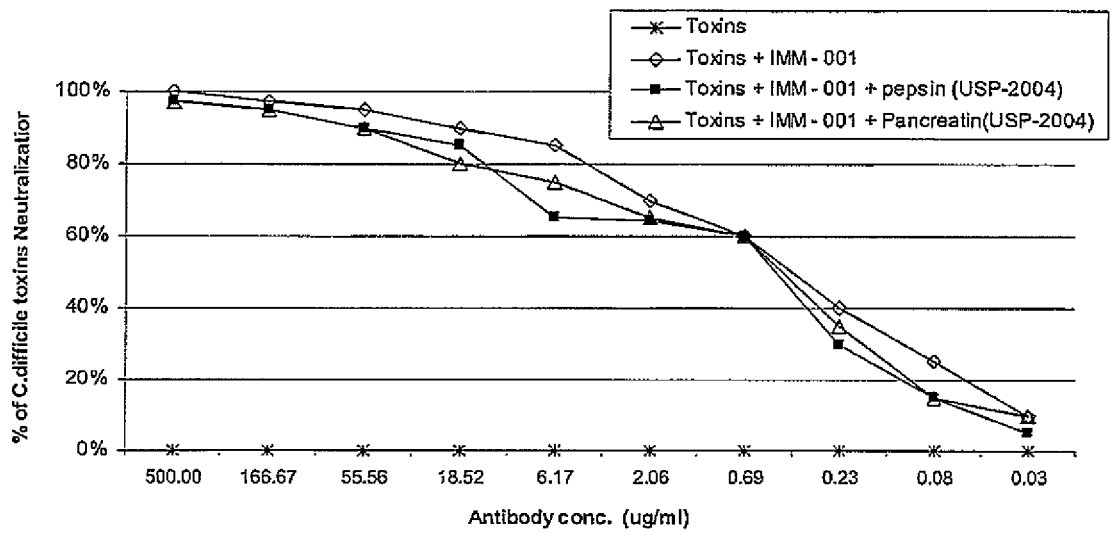

FIG. 9. Measurement of Gastric stability of IMM-001 formulation.

It has been demonstrated that toxin-neutralization ability of IMM-001 antibodies in its current formulation, as measured by cytotoxicity assay, is protected from digestive enzymes under simulated gastric and intestinal conditions.

Figure 10:
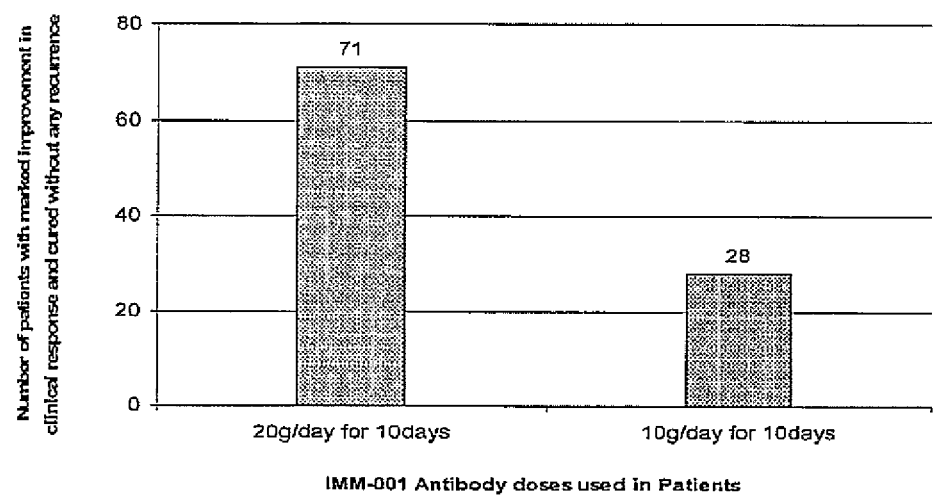

FIG. 10. Clinical efficacy of IMM-001 and Proof of concept in Patients with *C. difficile* infection treated with IMM-001—Dose Response Clinical Study.

Patients with *C. difficile* infections were enrolled in multicenter for proof of concept (POC) clinical studies. All patients enrolled were tested positive in a stool test for *C. difficile* culture and/or *C. difficile* toxins. 75 patients received 20 g of IMM-001 per day for 10 days and 28 patients received 10 g of IMM-001 per day for 10 days. Significant improvements in clinical symptoms were observed and negative stool test results were demonstrated in 99 patients after treatment.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Some aspects of the invention, including but not limited to some methods for generating the polyclonal antibodies of the invention, are disclosed in U.S. Pat. No. 7,713,527 (Filed: Sep. 18, 2006; Issued: May 11, 2010), U.S. Pat. No. 7,820,171 (Filed: Apr. 14, 2008; Issued: Oct. 16, 2010), Canadian Patent No. CA 2560283 (Filed: Sep. 18, 2006, Issued: Nov. 19, 2013), and Canadian Patent No. CA 2629790 (Filed: Apr. 14, 2008, Issued: Nov. 12, 2013), all of which are incorporated herein by reference.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and biospecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, biospecific antibody fragments and other fragments can also be synthesized by recombinant techniques.

It has been reported that the increased risk of recurrence has been associated with the failure of the immune system of the infected individual to mount an adequate antitoxin antibody response. Antibodies produced by the host against the *C. difficile* shown to be correlated with protection from recurrent *C. difficile* infections (Katchar, K. et al. 2007. Association between IgG2 and IgG3 subclass responses to toxin a and recurrent *Clostridium difficile*-associated disease. Clin. Gastroenterol. Hepatol. 5: 707-713; Kelly, C. P. and Kyne, L. 2011, The host immune response to *Clostridium difficile*. J. Med. Microbial. 60: 1070-1079). However, the ability to mount this immune response decreases with age; so the immune system of an old-age host may fail to protect against infections caused by *C. difficile* (Kee, V. R., 2012). Therefore, one strategy of the invention is to provide the protective antibodies orally to treat patients for protection against *C. difficile* infections.

Described herein is a polyclonal antibody composition prepared from eggs of immunized hens is used to treat *C. difficile* infections. As discussed below, respective groups of hens are immunized with Toxin A or Toxin B of *Clostridium difficile* or a *Clostridium difficile* spore preparation. The polyclonal antibodies are recovered, isolated or purified from eggs pooled from the immunized hens and the resulting powder is administered in a therapeutically effective amount to individuals infected with or suspected of being infected with *C. difficile*. Specifically, the polyclonal antibody composition comprises antibodies which will bind to *C. difficile* virulence factors and spores and will also block pathogenic effects of *C. difficile* Toxin A and Toxin B.

As will be appreciated by one of skill in the art, one of the problems encountered when treating a CDI with antibiotics is that *C. difficile* may form spores so as to resist the antibiotics; however, the antibiotics will disrupt the colonic flora of the host animal, thereby creating an environment suitable for CDI recurrence. However, the polyclonal antibody described herein not only neutralizes the toxins, it also binds to and interferes with the ability of *C. difficile* spores to bind to the mucosal lining, as demonstrated herein. Furthermore, the polyclonal antibody composition has been demonstrated to have efficacy at treating patients of all ages, including elderly patients and patients at higher risk of CDI and CDI recurrence. The polyclonal antibody composition is also well tolerated by human patients and has shown to be effective even against hypervirulent *C. difficile* strains.

The oral antibody therapy of the invention provides distinct advantages over other therapies for treatment of *C. difficile* infections, as it is safe without any toxicity and is able to inhibit the biological action of *C. difficile*.

Specifically, the polyclonal antibody composition provides a therapeutic and prophylactive treatment for *Clostridium difficile* infections or *C. difficile*-associated diarrhea and diseases. As discussed in the Examples, the polyclonal antibody composition has been demonstrated to significantly improve the clinical symptoms associated with CDI, as well as to cure the disease and eradicate *C. difficile* from the patient. That is, as discussed herein, the polyclonal antibody composition comprises polyclonal antibodies raised against *C. difficile* spores which remove the spores from the gastrointestinal tract of the patient, as evidenced by lack of *C. difficile* detection in stool samples from the patients, as discussed below. As discussed in the examples below, 103 patients to date have been successfully treated with the polyclonal antibody composition of the invention. Furthermore, as discussed in the examples, the disease severity ranged from severe diarrhea to pseudomembranous colitis and colitis, as many of the patients treated with the polyclonal antibody composition of the invention were those for whom antibiotic therapy had failed and there were no other treatment options.

As discussed herein, the polyclonal antibody composition was administered to patients by oral administration. Specifically, because the polyclonal antibody composition is formulated with ovalbumin, antibody degradation in the gut by gastric enzymes is significantly reduced, as discussed herein.

Furthermore, the polyclonal antibody composition is derived from human consumable eggs, which are safe for human consumption without any toxicity. The US FDA considers egg-derived products as GRAS (Generally Recognized as Safe). This is evidenced by the successful treatment of over 100 patients without side-effects, as discussed herein. It is also important to note that these patients had severe gastrointestinal infections and were still able to tolerate oral administration of the polyclonal antibody composition.

As discussed herein, this is possible because the polyclonal antibody composition comprises antibodies against Toxin A, Toxin B and *C. difficile* spores. Consequently, the composition targets the virulence factors of *C. difficile*, which are responsible for the symptoms associated with CDI and CDAD and also targets the spores of *C. difficile* which are responsible for transmission and recurrence of CDI. As demonstrated below, the polyclonal antibody composition is capable of effective neutralization of toxins, which damage the intestinal mucosa.

Furthermore, the antigens are prepared from full length Toxin A, Toxin B and *C. difficile* spores. In some embodiments, intact full length Toxin A, Toxin B and spores are used although embodiments in which immunogenic fragments thereof are used as antigens are also contemplated. As will be apparent to one of skill in the art and as discussed herein, the advantage of polyclonal antibody preparations compared to monoclonal antibodies is that the polyclonal antibody preparation comprises poly-specific antibodies which recognize and bind to multiple epitopes on a single target. Accordingly, the use of "full length" antigens is preferred for obvious reasons but is not necessarily an essential feature of the invention.

Furthermore, as shown in the examples, the polyclonal antibody composition comprises antibodies which bind to virulence factors and/or toxins from *C. difficile* clinical isolates with diverse genetic makeup, having different ribotypes and toxinotypes in an antibody dose-dependent manner, as discussed below.

As can be seen in the examples, the oral dosage and treatment regime used varied depending on the patient but was typically 10 or 20 g per day for 10 consecutive days.

In one aspect of the invention, there is provided a method of preparing a polyclonal antibody composition for treating or preventing or prophylactically treating a *Clostridium difficile* associated disease comprising:

a) inoculating a first group of egg-laying hens with an antigen prepared from *Clostridium difficile* Toxin A;

b) inoculating a second group of egg-laying hens with an antigen prepared from *Clostridium difficile* Toxin B;

c) inoculating a third group of egg-laying hens with an antigen prepared from *Clostridium difficile* spores;

d) collecting eggs laid by said first group, said second group and said third group; and e) recovering polyclonal antibodies from said collected eggs.

The antigens may be administered to the hens in combination with an adjuvant. In some embodiments the adjuvant is MONTANIDE-ISA-70™.

In some embodiments, the hens may be inoculated or immunized more than once prior to collection of the eggs.

In some embodiments, the polyclonal antibodies are recovered from the collected eggs by freeze-drying the eggs or by spray-drying the eggs.

Preferably, the polyclonal antibody composition has a reciprocal titer of <128,000.

As will be appreciated by one of skill in the art, each group of hens may comprise 5, 10, 15, 20, 30, 40, 50, 75, 100, 150, 200, 250, 500, 1000, 2000, 3000, 4000, 5000 or more hens.

Furthermore, unlike the difficulties encountered with the production of large quantities of colostrum-based or IVIg antibody products, the inventors have found that 1000 immunized chickens will produce 750 Kg of polyclonal antibody composition in a 2-month time period. As will be apparent to one of skill in the art, this corresponds to the therapeutic treatment of 3750 CDI patients at 10 g dosage daily for 10 days.

As will be appreciated by one of skill in the art, more hens in each group means lower potential variability between batches of the polyclonal antibody composition.

Specifically, each group of immunized hens will produce eggs containing polyclonal antibodies against *Clostridium difficile* Toxin A, Toxin B or spores for several months and as such, because of the number of immunized animals, the consistency of the polyclonal antibody composition will be less variable both within groups of hens immunized with the same antigen and compared to subsequent groups of immunized hens.

As will be appreciated by one of skill in the art, the collected eggs may be pooled prior to recovery of the polyclonal antibodies by freeze drying or spray drying. Alternatively, the polyclonal antibodies from each group may be recovered separately and then combined.

As will be appreciated by one of skill in the art, the Toxin A, Toxin B and spore antigens may be prepared using any suitable means known in the art, for example, using the methods exemplified in the Examples provided below. While in some embodiments, full-length toxins and intact spores are used as part of the antigen, immunogenic fragments of either one or both of the toxins and/or the spores may be used in antigen preparation, as discussed herein.

Thus, in one embodiment, the polyclonal antibody composition of the present invention comprises egg yolk antibodies that bind to and/or neutralize *C. difficile* Toxin A or a fragment thereof, *C. difficile* Toxin B or a fragment thereof, and that bind to *C. difficile* spores and effectively neutralize the spores by preventing and/or interfering with the ability of the spores to bind to the mucosal lining of the gastrointestinal tract of the infected host, as discussed below. As will be appreciated by one of skill in the art, the spores are responsible for transmission and recurrence of CDI. As such, polyclonal antibodies that bind to and prevent spores from adhering to the mucosal lining of the gastrointestinal tract of an infected host will if given prophylactically or to a patient suspected of or at risk of having consumed or contracted *C. difficile* spores cure CDI and/or prevent recurrence of CDAD, as discussed herein.

As demonstrated in the examples below, the polyclonal antibodies prepared herein demonstrate effective binding and neutralization of Toxin A, Toxin B and spores from a number of different *C. difficile* isolates. As will be apparent to one of skill in the art, this demonstrates the advantage of polyclonal antibodies compared to monoclonal antibodies as the various antibodies within the polyclonal antibody composition will bind to multiple neutralizing epitopes on the toxins and spores.

According to another aspect of the invention, there is provided the use of the polyclonal antibody composition described above to treat or prevent or prophylactically treat a *Clostridium difficile* infection and/or a *Clostridium difficile* associated disease, as discussed herein.

In one aspect of the invention, there is provided a method for treating or preventing or prophylactically treating a *Clostridium difficile* associated disease comprising administering to an individual in need of such treatment an effective amount of a polyclonal antibody composition, said polyclonal antibody composition being prepared by a method comprising:

a) inoculating a first group of egg-laying hens with an antigen prepared from *Clostridium difficile* Toxin A;

b) inoculating a second group of egg-laying hens with an antigen prepared from *Clostridium difficile* Toxin B;

c) inoculating a third group of egg-laying hens with an antigen prepared from *Clostridium difficile* spores;

d) collecting eggs laid by said first group, said second group and said third group;

e) recovering polyclonal antibodies from said collected eggs; and f) administering a therapeutically effective amount of the polyclonal antibodies to an individual in need of such treatment.

In another aspect of the invention, there is provided a polyclonal antibody composition for treating or preventing or prophylactically treating a *Clostridium difficile* associated disease characterized in that said polyclonal antibody composition being prepared by a method comprising:

a) inoculating a first group of egg-laying hens with an antigen prepared from *Clostridium difficile* Toxin A;

b) inoculating a second group of egg-laying hens with an antigen prepared from *Clostridium difficile* Toxin B;

c) inoculating a third group of egg-laying hens with an antigen prepared from *Clostridium difficile* spores;

d) collecting eggs laid by said first group, said second group and said third group; and e) recovering polyclonal antibodies from said collected eggs.

As discussed herein, the effective amount may be for example 2 to 40 g or 2 to 30 g or 2 to 20 g or 5 to 40 g or 5 to 30 g or 5 g to 20 g or 10 to g of the polyclonal antibody composition, as discussed herein.

The polyclonal antibody composition may be administered daily to the individual in need of such treatment until treatment has been concluded, as discussed herein. For example, the polyclonal antibody composition may be administered for a period of at least 7 days, 7-21 days, 7-10 days, 7-14 days, at least 10 days or 10-14 days.

In some embodiments of the invention, a polyclonal antibody preparation referred to herein as IMM-001, prepared as described above is provided and used.

Figure 1:
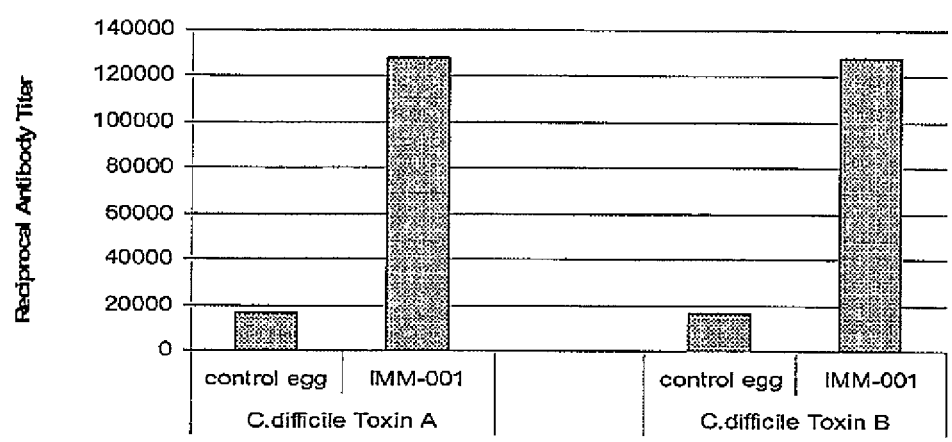
FIG. 1. IMM-001 Antibody Reactivity to *C. difficile* Toxin A and *C. difficile* Toxin B. ELISA plates were coated with *C. difficile* toxin A and *C. difficile* toxin B. Both controls (egg powder from chickens prior to immunizations with *C. difficile* antigens) and IMM-001 polyclonal antibodies were diluted to 1:140,000, and incubated with toxins on the plates to determine binding activity. IMM-001 showed strong positive reactivity against both *C. difficile* Toxin A and Toxin B at a dilution of 1:128,000, when control egg powder did not show any reactivity to any of the toxins.

The reactivity and specificity of IMM-001 was established by evaluating the binding characteristics against *C. difficile* toxin A and *C. difficile* toxin B antigens using an ELISA immunoassay (FIG. 1). The result shows that IMM-001 demonstrated strong reactivity (binding) to *C. difficile* Toxin A and B in a dose dependent manner.

Figure 2:
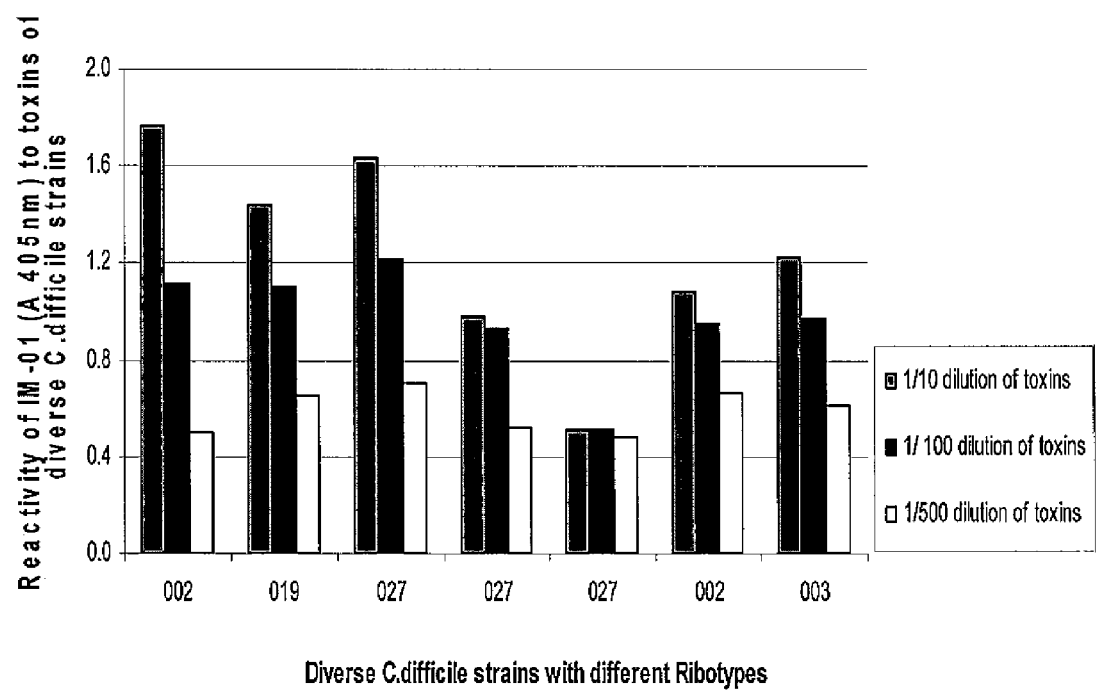
FIG. 2. Reactivity of IMM-001 antibodies to *C. difficile* toxins produced in culture supernatant by genetically diverse *C. difficile* strains.

Functional activities were evaluated in vitro, using cell-based assays, to determine neutralization ability of IMM-001 against Toxin A and Toxin B-mediated cytotoxicity (FIG. 2). The result shows that IMM-001 neutralized *C. difficile* Toxin A and Toxin B-mediated cytotoxicity in vitro in a dose dependent manner.

As discussed herein, one aspect of the invention provides a method of neutralizing, inhibiting, blocking, reducing, ameliorating, curing, or treating *C. difficile* infection or a *C. difficile*-associated disease in a subject in need thereof, comprising administering to the subject an effective amount of the above-described polyclonal antibodies in a therapeutically effective amount that is sufficient to neutralize, inhibit, block, reduce, ameliorate, cure, or treat *C. difficile*-associated disease or CDAD, including symptoms such as mild to severe diarrhea and in some cases associated with severe, life threatening complications, such as pseudomembranous colitis, toxic megacolon, bowel perforation, sepsis and death, in the subject.

As discussed herein, the recurrence rate of a *C. difficile* infection is very high because of the ability of *C. difficile* to exist as spores within the animal host and to return to vegetative growth once growth conditions are more favorable, that is, once antibiotic therapy has ceased.

However, the polyclonal antibody composition, designated herein as IMM-001, in addition to comprising antibodies which bind to and neutralize toxins A and B, thereby ameliorating symptoms associated with *C. difficile* associated diseases or a *C. difficile* infection, also comprises antibodies against *C. difficile* spores. The binding of these antibodies to the spores promotes removal of the spores from the animal host gastrointestinal tract.

Furthermore, because the composition comprises polyclonal antibodies, multiple epitope targets on toxin A and B and the spores are bound by the antibodies of the composition. As a result, variations between strains are not as much of a concern as it can be with monoclonal antibody preparations which recognize only a single epitope.

In addition, the polyclonal antibody material is prepared from the eggs of a large number of immunized animals over a long period of time, thereby reducing concerns regarding the reproducibility and consistency of the polyclonal antibody material.

Finally, the polyclonal antibody material is prepared with a sufficiently high titer that therapeutic treatment of humans is possible, as discussed herein. Specifically, as discussed herein, the polyclonal antibody composition has a reciprocal titer of <128,000.

Thus, in summary, the polyclonal antibody composition of the present invention provides a distinct advantage over other therapies in that it is able to inhibit the biological action of toxins A and B of *C. difficile* and the spores of *C. difficile*. Moreover, the polyclonal antibody material of the present invention can be produced with very high titres. The antibodies of the present invention may also be used prophylactically to prevent the onset of CDI in a patient known to have or at risk of having become infected by *C. difficile*, as discussed herein.

As discussed herein, the *C. difficile* may be an antibiotic resistant and/or hypervirulent strain. For example, the *C. difficile* strain may be CCL678, HMC553, Pitt45, CD196, montreal 5, montreal 7.1, MH5, Pitt2, CCL14137, UVA17, UVA30/TL42, or Pitt7.

The invention also embraces a corresponding method for prevention or treatment of CDI, said method comprising oral administration of the polyclonal antibody composition of the present invention to a patient in need of such treatment. The patient in need of such treatment can be infected with *C. difficile*, or have a symptom of *C. difficile* (for example, mild self-limiting diarrhoea, abdominal pain, fever and loss of appetite or life-threatening conditions such as pseudomembranous colitis and cytotoxic megacolon) or have a predisposition towards *C. difficile* infection (for example, undergoing treatment with antibiotics, having experienced *C. difficile* and/or at risk of relapse, or exposed to a second individual who has shown the clinical symptoms associated with *C. difficile* infection) or an individual who is at risk of *C. difficile* infection, for example, an elderly person for example of age 60 or higher or 65 or higher; or 70 or higher an immuno-compromised individual; or a patient in a long term care facility. The present invention provides an effective means for preventing, suppressing, treating or prophylactically treating CDI or a symptom thereof. For example, the polyclonal antibodies may be administered to an individual who has tested positive for *C. difficile* but is asymptomatic or who is considered likely to have or is suspected of having been infected with *C. difficile*.

In one embodiment, said method of treating CDI comprises oral administration of the polyclonal antibody composition of the present invention to a patient infected with *C. difficile*, or suffering from the symptoms of CDI. This can be accomplished using a therapeutically effective amount of the antibodies. Such administration may be effected by repeated administrations of antibody compositions of the present invention, for a prolonged period of time.

A therapeutically effective amount refers to the amount of the antibody, which when administered to a patient for treating CDI or CDAD, or at least one of the clinical symptoms of CDI or CDAD, is sufficient to affect such treatment of the disease, or symptom. The therapeutically effective amount can vary depending, for example, on the infection, and/or symptoms of the infection, severity of the infection, and/or symptoms of the infection, the age, weight, and/or health of the patient to be treated, and the judgment of the prescribing physician. An appropriate therapeutically effective amount in any given instance may be ascertained by those skilled in the art or capable of determination by routine experimentation.

In another embodiment, said method of preventing CDI comprises oral administration of the polyclonal antibody composition of the present invention to a patient to provide passive immunity against CDI. This can be accomplished using a prophylactically effective amount of the antibodies prior to the onset or in the very early stages of CDI. Such administration may be effected by repeated administrations of antibody compositions of the present invention, for a prolonged period of time.

In one embodiment, the subject to be treated or protected is a subject in one or more of the following category: hospitalised; over 60 or 65 or 70 years' old; receiving broad-range spectrum antibiotics; having previous CDI history/infection; having close proximity to symptomatic CDI patients; having mild-to-moderate disease severity; presenting as asymptomatic but considered at high risk of relapse (eg. because of one or more relapse episodes); having close proximity to CDI outbreak areas or patients. As such, in these embodiments, the polyclonal antibody composition is administered to a subject who is asymptomatic but who is susceptible to or at risk of contracting CDI or developing CDAD.

The dosage ranges for administration of the antibodies of the present invention are those to produce the desired therapeutic effect. It will be appreciated that the dosage range required depends on the precise nature of the composition, the nature of the formulation, the age of the patient, the nature, extent or severity of the patient's condition, contraindications, if any, and the judgement of the attending physician.

As discussed in the examples, daily dosages of 10 g and 20 g of the IMM-001 polyclonal antibody powder have been administered to human patients suffering from CDI and/or CDAD for a period of 10 days and have successfully treated these human patients. While these dosages have been well tolerated by patients suffering from severe gastrointestinal trauma, other suitable effective amounts may be determined through routine experimentation and optimization. Variations in these dosage levels can be adjusted using standard empirical routines for optimisation as well as in consideration of other factors such as for example the age, general condition and severity of symptoms of the subject, as discussed herein.

As discussed herein, the dosage of 10 g or 20 g per day was selected based on the data from a preclinical animal study wherein *C. difficile* infected piglets were treated. Each piglet (1.8 Kg-2.00 Kg) received 0.6 g of IMM-001 per day. Based on an average human body weight of 70 Kg, about 35× that of the pigs, this converts to approximately 20 g. Alternatively, the dosage amount may be calculated as 0.3 g per Kg of the subject or individual or patient. However, as discussed above, other amounts may be administered, depending on multiple factors, including but by no means limited to the age, weight, general condition and severity of symptoms of the individual.

Furthermore, the dosage period may be varied and the 10 days provided above should be viewed as a guideline and not as mandatory. For example, the polyclonal antibody composition may be administered daily at an effective amount of 5 g to 20 g to an individual in need of such treatment for a period of at least 7 days, 7-21 days, 7-14 days, 7-10 days, at least 10 days or 10-14 days.

As will be appreciated by one of skill in the art, the attending physician can determine how long administration of the polyclonal antibody composition should be continued, for example, until the severity of symptoms has been reduced or until *C. difficile* is no longer detectable.

IMM-001 may be administered directly to the patient as a powder or the powder may be dissolved in a suitable liquid vehicle, for example, milk or water. As will be appreciated by one of skill in the art, other suitable delivery systems are well known in the art and are within the scope of the invention.

It is also within the scope of the invention to use the antibodies of the invention in oral therapeutic methods for the prevention or treatment of CDI in combination with one another, or as an adjunct to, or in conjunction with, other established therapies normally used in the treatment in CDI. For example, the antibodies of the present invention may be administered in conjunction with a suitable antibiotic. The antibiotic may be for example but by no means limited to metronizadole, vancomycin, fidaxomicin, nitazoxanide rifaximin, ramoplanin or combinations thereof. The combination treatment may be carried out in any way as deemed necessary or convenient by the person skilled in the art and for the purpose of this specification, no limitations with regard to the order, amount, repetition or relative amount of the compounds to be used in combination is contemplated. As discussed herein however, co-administration of the polyclonal antibody composition with an anti-*C. difficile* antibiotic is not an essential aspect of the invention as the polyclonal antibody composition has treated over 100 human patients without co-administration with antibiotics. Furthermore, as discussed in the examples, in many of these human patients, antibiotic therapy had failed to cure the CDI/CDAD and had been discontinued.

In other embodiments, an antacid component may be added. In use, said antacid component helps protect the antibodies from the highly acid gastric environment that exists within a patient.

An antacid is any substance, generally a base or basic salt, which counteracts stomach acidity. In other words, antacids are stomach acid neutralizers that raise the stomach pH, ideally above pH 4.0, for a limited time period Antacids perform a neutralization reaction, i.e. they buffer gastric acid, raising the pH to reduce acidity in the stomach.

Examples of suitable antacids for use in the present invention include, but are by no means limited to: Prevacid, Prilosec, gastric-acid suppressant, aluminium hydroxide (eg. Amphojel, AlternaGEL); magnesium hydroxide (e.g. Philips' Milk of Magnesia); aluminum hydroxide with magnesium hydroxide (e.g. Maalox, Mylanta, Diovol); Aluminum carbonate gel (eg. Basaljel); calcium carbonate (eg. Alcalak, TUMS, Quick-Eze, Rennie, Titralac, Rolaids); sodium bicarbonate (eg. bicarbonate of soda, Alka-Seltzer); magnesium carbonate; magnesium trisilicate; hydrotalcite (eg. Mg6Al2(CO3)(OH)16.4(H2O); Talcid); bismuth subsalicylate (e.g. Pepto-Bismol); alginates (e.g. sodium alginate, alginic acid); magaldrate with simethicone (eg. Pepsil); any of the above in combination with simethicone for example Asilone, which has three active ingredients, aluminium hydroxide and magnesium oxide neutralise the acid removing the cause of the pain, and dimethicone.

The invention will now be further elucidated by way of examples; however, the invention is not necessarily limited by the examples.

EXAMPLE 1

Manufacturing of Egg-Derived Polyclonal Antibodies IMM-001

IMM-001 is an oral polyclonal antibody therapy for the treatment of *Clostridium Difficile* Infection (CDI). IMM-001 is produced in chicken eggs following the immunization of laying hens with specific *C. difficile* virulent factor antigens: *C. difficile* toxin A and toxin B, and *C. difficile* spores.

Preparation of Immunogens

A *Clostridium difficile* strain isolated from the stool sample of a *C. difficile* infected patient was grown in Brain Heart Infusion (BHI) medium for 16-18 hrs at 37° C. in an anaerobic chamber. The bacteria were harvested by centrifugation to collect the bacterial pellet. For production of spore antigen, *C. difficile* was grown in BHI medium for 16-18 hrs at 37° C. in an anaerobic chamber, followed by spreading the culture on Columbia blood agar plates. The plates were then incubated for 5-7 days, at 37° C. in the anaerobic chamber. The spores were harvested in RO water, washed in RO water, centrifuged at 1400 RPM for 10 minutes, resuspended in RO water and stored in a freezer.

For preparation of immunogen, 1% formaldehyde was added to the spore suspension and incubated at 37° C. for 24 hours and lien dialysed in PBS at 4° C. overnight.

For production of *Clostridium difficile* toxins, *C. difficile* was grown in BHI medium for 5 days at 37° C. in the anaerobic chamber. The purification of the toxin A and toxin B antigens was performed as described by Fu et al 2004, World J. Gastroenterol 10: 2756-2758. The culture supernatant was removed by centrifugation at 800× for 20 minutes and the toxin containing proteins in the supernatant were then subjected to ammonium sulfate precipitation, by adding 60% of ammonium sulfate. Following incubation at 4° C. overnight, the precipitate was dissolved in 20 mM Tris-HCl buffer pH 7.5 and dialysed against 10 mM acetate buffer pH 5.5 at 4° C. overnight. After dialysis, the precipitate containing toxin A and B was separated by centrifugation and dissolved in 4 mL of 50 nM Tris-HCl buffer. Finally, Toxin A and toxin B were purified by anion-exchange column chromatography using DEAE-Toyoperl and the protein peak containing toxins were eluted with a gradient of 200-400 mM of NaCl 50 nM of Tris-HCl. The purified toxins were concentrated and stored in a freezer until use.

For preparation of immunogens, toxin A and toxin B were fixed with 0.4% of formaldehyde by incubation at 37° C. for 24 hours. Subsequently, the fixed-toxins were then dialysed against PBS at 4° C. overnight.

Immunization of Laying Hens for Production of IM-01 Polyclonal Antibody-Containing Eggs The preparation of the *C. difficile* vaccine, (antigen+MONTANIDE-ISA-70™ adjuvant), was carried out for the immunization of the hens. The *C. difficile* antigen+adjuvant were prepared by the mixing of the *C. difficile* antigen and the adjuvant at a ratio of 30:70 respectively. The mixture was homogenized to make a uniform suspension prior to the vaccination of the hens.

Pathogen-free, healthy white Bovins hens, 24-25 week-old, were vaccinated with a 0.5 mL of *C. difficile* antigen-adjuvant, with 0.25 mL injected intramuscularly into each side of the pectoral muscles. The vaccination was repeated three times with 3-week intervals between each injection for a total of three vaccinations.

Production of IM-01-Egg-Derived Polyclonal Antibodies

Antibody eggs were collected for the first time 3 weeks post-vaccination. These eggs were washed with 0.5% Sodium hypochlorite, broken and the freeze-dried or spray-dried to produce IMM-001 polyclonal antibodies. The levels of *C. difficile* polyclonal antibodies in these in-process egg samples were tested by ELISA to determine the reactivity against *C. difficile* antigen(s).

Purity and safety are tested for each batch with the same microbiological techniques used for eggs intended for human consumption. This includes *Salmonella* spp., Coliform and standard plate count as required by Health Canada and CFIA. Description and Composition of the polyclonal antibody composition IMM-001 is a powder for oral suspension. IMM-001 is composed of ovalbumin (egg white) and egg yolk. No other excipients are added.

EXAMPLE 2

Specificity and Reactivity of Polyclonal Antibodies IMM-001 to *Clostridium difficile* Toxins Using ELISA Assays Shown in Figure-1

Specificity and reactivity of IMM-001 to *C. difficile* toxin A and toxin B antigens was demonstrated using 96-well polyvinyl chloride (PVC) flat bottom ELISA plates coated with 0.2 μg of purified toxin A or toxin B in 100 μL of carbonate-bicarbonate coating buffer each well. The toxin-coated plates were incubated at 4° C. for 16-18 hrs and washed with washing buffer (PBS+0.5% Tween 80). Non-specific sites were blocked after incubation with the blocking buffer (1% skim milk in PBS), the wells were washed with washing buffer and incubated at 37° C. br 2 hours with 100 μL per well of the diluted IMM-001 polyclonal antibodies in egg powder or control egg powder derived from the chicken eggs prior to vaccination. Samples were diluted to determine antibody titers in each of the test and control samples. Subsequently, the antigen-antibody interaction was detected after incubation with alkaline phosphatase-conjugated rabbit anti-chicken IgG at 37° C. for 2 hours, followed by incubation with the alkaline-phosphatase substrate. The reactivity was determined by measuring the absorbance at 405 nm.

As illustrated in FIG. 1, control egg demonstrated very weak reactivity against *C. difficile* toxin A and toxin B antigens with a reciprocal antibody titer ≤16,000. In contrast, the IMM-001 polyclonal antibodies showed very strong reactivity against *C. difficile* toxin A and toxin B with a reciprocal antibody titer <128,000, demonstrating that IMM-001 egg-derived polyclonal antibodies specifically binds to the *C. difficile* toxin antigens.

Spectrum of Reactivity of Polyclonal Antibodies IMM-001 to Toxins Produced by Genetically Diverse *C. difficile* Strains Shown in Table 1

*Clostridium difficile* is a widely distributed pathogen with multiple strain types as determined by PCR ribotyping. Ribotype 027 isolates were found to be the most common strains identified and distributed throughout the North America and some countries in Europe. Other *C. difficile* ribotypes also have been detected from disease patients from North America, Europe, Asia and Australia (Cheknis, A. K. et al., 2009, Anaerobe 15: 230-233).

A strain type classified as NAP/B1/027 was found to be responsible for more than half of the *C. difficile* infected cases with high morbidity and mortality in North America and Europe (Merrigan, M. et al. 2010).

*C. difficile* isolates of NAP/B1/027 have been implicated as hypervirulent strains and linked with disease severity as well as hospital outbreaks worldwide. It has been suggested that these hypervirulent strains produce larger amount of toxins relative to the non-hypervirulent strains, since production of toxins correlated well with the presence and the type of toxin genes. Although the majority of ribotypes with variant strains produced both toxins, many strains produce only TcdB (A−B+) (Rupnik, M. et al., 2001, Microbiology 147: 439-447; Rupnik, M. 2008, FEMS Microbiol. Rev. 32: 541-555. Aside from the two toxin genes (tcdA and TcdB), there are three other genes within the PacLoc: tcdC, tcdR and tcdE (Braun, V et al., 1996, Gene 181: 29-38). tcdC, which encodes a negative regulator of toxin expression, is highly variable. There are four types of deletions present in different toxinotypes.

The reactivity of IMM-001 polyclonal antibodies was assessed against toxins produced in vitro in the culture supernatant by genetically diverse *C. difficile* strains isolated from patients with *C. difficile* infections. A fixed number of spores from various clinical isolates of *C. difficile* strains were grown in Brain Heart Infusion (BHI) medium for 72 hours. The culture supernatant was separated from the bacterial mass by centrifugation of the broth at 4,000 RPM for 20 minutes.

The ELISA plates were coated with culture supernatant containing C. difficile toxins from diverse C. difficile strains. The toxin-coated ELISA plates were treated in a similar fashion, as described above. Antibody reactivity with toxins was determined after incubation with 1:2000 dilution of control egg powder obtained from un-vaccinated chickens or IMM-001 antibodies. Finally, the toxin-antibody reaction was detected following incubation with alkaline phosphatase-conjugated rabbit anti-chicken IgG at 37° C. for 2 hours, followed by incubation with the alkaline-phosphatase substrate. The reactivity was determined by measuring the absorbance at 405 nm.

Toxin-Dose Dependent Binding of Polyclonal Antibodies, IMM-001 to Toxins Produced in Culture Supernatant of Diverse C. difficile Strains Although hypervirulent strains such as NAP/B1/027 have been implicated to produce larger amount of toxins relative to the non-hypervirulent strains, it has also been reported that the amounts were not significantly different from that of non-hypervirulent strains (Merrigan, M. et al 2010).

Consequently, the reactivity of IMM-001 polyclonal antibodies was tested against C. difficile toxins present in the diluted culture supernatants produced by genetically diverse C. difficile strains, with four different ribotypes: 002, 003, 019 and 027. ELISA plates were coated with 10, 100 and 500 times diluted culture supernatants obtained from seven different C. difficile strains. The toxin-coated ELISA plates were treated in a similar fashion as described above. Antibody reactivity with toxins was determined after incubation with 1:2000 dilution of control egg powder obtained from un-vaccinated chickens or IMM-001 antibodies. Finally, the toxin-antibody reaction was detected following incubation with alkaline phosphatase-conjugated rabbit anti-chicken IgG at 37° C. for 2 hours, followed by incubation with the alkaline-phosphatase substrate. The reactivity was determined by measuring the absorbance at 405 nm and the result is shown in Table 1. The results demonstrate that IMM-001 polyclonal antibodies showed strong reactivity (OD value at 405 nm 0.92-1.8) to toxins generated in culture supernatant from genetically diverse C. difficile strain with ribotypes: 004, 002,019,003,NAP/B2/027 and toxinotypes: 21, 0, 6, 9, 8, 3 and 2.

Additional results are shown in FIG. 2. IMM-001 polyclonal antibodies showed strong reactivity against toxins produced by all seven clinical isolates of C. difficile of four different ribotypes, 002, 003, 019 and 027. However, the reactivity was strongest with the 1/10 dilution and weakest with the 1/500 dilution of culture supernatant.

It was concluded that clinical isolates of C. difficile produced variable amounts of toxins in vitro in the culture supernatants and IMM-001 antibodies exhibited strong reactivity, but the reactivity was determined to be toxin-concentration dependent.

Binding Reactivity of IMM-001 Polyclonal Antibodies to Spores Produced by Genetically Diverse C. difficile Strains as Shown in Table 2

Although the toxins are responsible for symptoms of the disease, endospore formation is also an important factor that contributes to the disease transmission and recurrence of disease. Spores can survive, germinate, and proliferate in the gut following exposure to antibiotic treatment (Carlson, P. E. et al. 2013). Since C. difficile strains exhibited considerable inter-strain heterogeneity, various toxigenic clinical isolates were selected with genetic diversity, based on ribotype and toxinotype, in order to determine reactivity of IMM-001 antibodies to the spores produced by these diverse C. difficile strains.

ELISA plates were coated with 0.4 µg/mL of spore antigen and incubated overnight at 4° C. The plates were washed as described above. To determine antibody reactivity to spores, spore antigen-coated ELISA plates were incubated with either control egg powder from un-vaccinated chickens or IMM-001 antibodies at 1:4000 dilutions, followed by incubation with alkaline phosphatase-conjugated rabbit anti-chicken IgG. Subsequently, the antigen-antibody interaction was detected after incubation with the substrate. The reactivity was determined by measuring the absorbance at 405 nm.

It was demonstrated that the control egg powder showed weak reactivity ($A_{405}$<0.3) against C. difficile spores. In contrast, IMM-001 antibodies showed strong reactivity ($A_{405}$ 0.87-2.25) against C. difficile spores of genetically diverse origin, specifically, 10 different strains and 5 different ribotypes. The results are shown in Table 2.

It was concluded that IMM-001 antibodies can bind to spores generated by genetically diverse C. difficile strains.
Binding of IMM-001 Polyclonal Antibodies to C. difficile Bacteria of Genetically Diverse Origin Shown in Table 3

To determine the binding pattern of IMM-001 to C. difficile bacteria with genetically diverse origins, ELISA plates were coated with formalin-fixed C. difficile bacteria, 0.3 µg/100 µL/well, following the method described above. The ELISA plates were incubated 16-18 hours at 4° C., then washed and further incubated with a fixed concentration at 1:4,000 dilutions of IMM-001 antibodies. Subsequently, the plates were washed and further incubated with alkaline phosphatase-conjugated rabbit anti-chicken IgG. The antigen-antibody interaction was detected after incubation of the plates with the substrate and absorbance at 405 nm was measured. The results are shown in Table 3.

It was concluded that IMM-001 antibodies exhibited strong reactivity ($A_{405}$ 0.92-1.8) to C. difficile of diverse origin, when the control showed very weak reactivity ($A_{405}$<0.38).

The overall conclusion is that egg-derived polyclonal antibodies IMM-001 demonstrated strong reactivity to C. difficile virulent antigens of genetically diverse clinical isolates of C. difficile strains.

EXAMPLE 3

Assessment of Efficacy of IMM-001 Polyclonal Antibodies In Vitro Toxin Neutralization Ability of IMM-001 Antibodies Using IMR-90 Cell Line Based Assay Shown in FIGS. 3,4 & 5

The cellular cytotoxicity assays were designed to determine the functional activity and mode of action of IMM-001 antibodies, since the IMM-001 antibodies recognized C. difficile toxin antigens in binding studies discussed above.

The human lung fibroblast cell line, IMR-90, cell-based in vitro assay was used to determine C. difficile toxin neutralizing ability of IMM-001, since IMR-90 cells are sensitive to both toxin A and toxin B. Briefly, IMR-90 cells ($1 \times 10^5$/well) were incubated with C. difficile toxin A&B alone or toxin A&B+IMM-001 antibodies for 24 hours at 37° C. The cytopathic effects were determined by observing the percentage of cells that had become rounded in the presence of the toxins. When there is no cytopathic effect, i.e. cells that had not become rounded with toxin in presence of antibodies, toxin was considered 100% neutralized.

As shown the results in FIGS. 3, 4 and 5, no toxin neutralization activity was detected when the cells were incubated with toxin alone. In contrast, maximum neutralization activity (100%) was achieved when the toxin was mixed with IMM-001 antibody concentration at 6.17 μg/mL or higher. However, the toxin neutralization ability diminished to zero when the lowest amount of IMM-001 antibody (0.06 μg/mL) was added to the toxin.

It has been concluded that IMM-001 egg-derived polyclonal antibodies are capable of neutralizing the cytopathic effects mediated by *C. difficile* toxin A and toxin B on IMR-90 cells in vitro and the efficacy of toxin neutralization is IMM-001 antibody concentration-dependent.

EXAMPLE 4

Spectrum of Toxin Neutralizing Potency of IMM-001 with Toxins Produced by Genetically Diverse *C. difficile* Strains in IMR-90 Cell Line Based Assay Shown in Table 4

Since *C. difficile* exhibited considerable inter-strain heterogeneity in the genes encoding toxin A and B, these studies were undertaken to determine the toxin neutralization ability of IMM-001. A panel of genetically diverse *C. difficile* strains comprised of seven toxigenic clinical isolates with four different ribotypes was selected to assess ability of IMM-001 antibodies to neutralize toxins produced by these strains.

The cell-based assay was same as described above, except the toxin source. The culture supernatant from various *C. difficile* strains were used as toxin sources in this study, instead of the purified toxin from VPI 10463 that was used in the previous example. The IMR-90 cell-based assay was performed to determine the antibody concentration needed for 100% neutralization of toxins produced by these diverse strains.

It was concluded from the results that the antibody concentration needed to neutralize 100% toxin neutralization varied with the toxins produced in culture supernatant by diverse *C. difficile* strains. The highest amount 300 μg/mL and lowest amount 0.7 μg/mL of IMM-001 antibodies is needed to neutralize 100% cytopathic activity mediated by toxins produced by genetically diverse *C. difficile* strains, as shown in Table 4.

Efficacy of IMM-001 in neutralizing toxins from *C. difficile* hypervirulent NAP/B1/027 strain using T-84 cell line based assay is shown in FIG. 6.

As the IMR-90 cell line is considered to be sensitive to *C. difficile* toxins A and B, the human colonic tumor cell line, T-84, is considered to be more sensitive to *C. difficile* toxin A. A study was designed to confirm the efficacy of IMM-001 antibodies at neutralizing toxins produced by hypervirulent *C. difficile* strain NAP/B1/027, using a cell-based assay with T-84 cells.

The T-84 cells were incubated with either *C. difficile* toxins A and B alone or in combination (toxin A & B+polyclonal antibodies) for 24 hours at 37° C. The cytopathic effects were determined by observing the percentage of cells that had become rounded.

It was concluded from the results in FIG. 6, that toxin A and B individually demonstrated 100% cytopathic effect with no toxin neutralization on T-84 cells. *C. difficile* toxin+ control IgY in normal egg showed 85-90% cytopathic effect with 10-15% toxin neutralization on T-84 cells. In contrast, following incubation with toxin A & B+IMM-001 antibody demonstrated 0% cytopathic effect with 100% toxin neutralization. Furthermore, the toxin neutralization ability of IMM-001 antibody is determined to IMM-001 antibody dose-dependent.

EXAMPLE 5

Assessment of In Vitro Growth Inhibition Activity of IMM-001 Polyclonal Antibodies As *C. difficile* spores play a key role in the colonization, transmission and pathogenesis of CDI, experiments were designed to determine efficacy of IM-01 antibodies in vitro. *C. difficile* spores from 3 different isolates of hypervirulent *C. difficile* strain NAP/B1/027 were incubated with control antibodies (IgY) or IMM-001 antibodies for 24 hours to determine antibody effect on growth of *C. difficile*.

As shown in FIG. 7, that the 90-260 colonies were detected after incubation of a fixed number of *C. difficile* spores with control material, and the spore multiplication rate was determined to be different among the three hypervirulent strains. In contrast, only 5-20 colonies were detected following incubation of the same number of spores of the three genetically different *C. difficile* hypervirulent strains with IMM-001 antibodies.

Based on the results shown in FIG. 8, it was concluded that IMM-001 antibodies inhibited >80% growth of all the three *C. difficile* isolates of NAP/B1/027.

EXAMPLE 6

Assessment of IMM-001 Antibodies on Inhibition of Adhesion of *C. difficile* to Caco-2 Cells as Shown in Table 5

Although the role of toxin A and toxin B in pathogenesis of *C. difficile* infection is established, the exact sequence of pathological events leading to disease is not well understood, particularly on adhesion on human intestinal mucosa.

We studied the effect of IMM-001 polyclonal antibodies on adhesion of *C. difficile* bacteria to epithelial cells in vitro by using human colonic epithelial cell line Caco-2. This cell-line closely resembles small intestinal epithelial cells and has been used to study mechanisms of adherence and invasion of many pathogenic bacteria.

To quantify the effect of IMM-001 polyclonal antibodies on inhibition of *C. difficile* attachment to Caco-2 cell, cells were cultured and maintained using the ATCC protocol. Caco-2 cells were grown in cover slips in 24-well plate for 48 hours. Then medium from each well was removed, and Caco-2 cells were incubated with 100 μL of *C. difficile* bacteria of NAP/B1/027 ($10^7$ cfu/mL) in presence of 100 μL control material or of IMM-001 antibodies at 1 mg/ml, 0.5 mg/ml or 0.25 mg/mL for 2 hours at 37° C. Following incubation, Caco-2 cells were then rinsed with PBS to remove non-adherent bacteria. Cell-associated bacteria were fixed with methanol and stained with Giemsa. Once the cover slips were dried, the number of adherent *C. difficile* bacteria was enumerated per field under microscope and the numbers were counted in 26 fields for each cover slip.

As shown in the results, in Table 5, the average number of *C. difficile* bacteria detected in each field following incubation with control egg powder (IgY) ranged from 29.7-54.1. In contrast, the number of *C. difficile* bacteria detected after incubation with IMM-001 polyclonal antibodies was much lower, ranging from 13.9-16.1 per field. The highest inhibition of *C. difficile* adhesion to Caco-2 cells (73%) was achieved after incubation with IMM-001 antibodies at 0.25 mg/mL.

Based on the results shown in Table 5, it was concluded that IMM-001 antibodies inhibited 73% adhesion of hypervirulent *C. difficile* isolate of NAP/B1/027 strain onto Caco-2 cells.

EXAMPLE 7

Formulation of IM-01 Polyclonal Antibodies and Assessment of Gut Stability for Oral Administration as Shown in FIG. 9

The limitations of oral administration of antibodies are mainly due to degradation by proteolytic enzymes, such as Trypsin and Cymotrypsin, present in the gut. The proteolytic enzymes present in digestive secretions block large molecules, such as antibodies, from reaching the gut and the colon, where IMM-001 is required to interact with *C. difficile* toxins and spores. The proteolytic enzymes in digestive secretions are one of the factors that inhibit optimal amounts of antibody from reaching the gut.

It has been demonstrated in several studies that ovalbumin present in chicken egg white is a potent inhibitor of the proteolytic activity of trypsin/chymotrypsin and can protect the antibody molecules from the digestive enzymes in gut.

IMM-001 is produced and formulated with egg white that includes ovalbumin for protection from the enzymatic digestion in gut. In order to confirm the gut stability of IMM-001, experiments were designed to determine gastric stability of IMM-001 in vitro.

Formulations were assessed for gastric stability by exposure to simulated gastric conditions. Simulated gastric and intestinal conditions were prepared using a protocol described in Pharmacopeial Convention Council of Express (2004) 27, volume 22 p 2728. Antibody formulation IMM-001 was mixed with a solution of 3.2 mg/ml pepsin in 30 mm NaCl at pH 1.2, in the ratio of 1 part pepsin solution to 250 parts of antibody solution and incubated for 360 minutes at 37° C. Similarly, IMM-001 antibody was mixed with solution of 10 mg/ml pancreatin in 50 mM potassium phosphate buffer at pH 6.8, in the ratio of 1 part of pancreatin solution to 50 parts antibody solution and incubated for 360 minutes 37° C.

Subsequently, antibody-mediated toxin neutralization activity was measured before and after enzymatic treatment of IMM-001 antibodies in the IMR-90 cell based assay as described elsewhere herein, to assess functional integrity of the polyclonal antibodies of IMM-001.

As shown in FIG. 9, the toxin neutralization ability of IMM-001 antibodies was not altered even after treatment with pepsin and pancreatin.

It was concluded that, since toxin-neutralization ability had not been altered by proteolytic enzymes, IMM-001 in its current formulation is protected from digestive enzymes under simulated gastric and intestinal conditions.

EXAMPLE 8

Antibody Dose Selection for Treatment of Patients with *C. difficile* Infections, Efficacy of IMM-001, *C. difficile* Egg Derived Polyclonal Antibodies in Pigs

*Clostridium difficile* is a ubiquitous bacterium in the environment that has been recognized as an important emerging pathogen in both humans and animals. Veterinary medicine has highlighted the role of animals as reservoirs for *C. difficile*. In recent years, *C. difficile* has been identified as causing neonatal diarrhea in pigs (Songer, J. G. and Uzal, F. A. 2005, J. Vet. Diagn. Invest. 17: 528-536; Squire, M. M. et al., 2013, Emerg. Infect. Dis. 19: 790-792).

A proof-of-concept study was planned in animals to determine efficacy of IMM-001 in the prevention and treatment of *C. difficile*-induced diarrhea in piglets, since 3-7 day old piglets are highly susceptible to *C. difficile* diarrhea and *C. difficile* enteritis.

*C. difficile* infected piglets (15) on a farm in Minnesota, Minn., were used to measure the efficacy of IMM-001 against *C. difficile* enteritis. The *C. difficile* infection was confirmed by *C. difficile* toxin positive stool results from Veterinary Diagnostic Laboratory. Subsequently, *C. difficile* infected piglets were fed 0.6 g of IMM-001 once a day for 2 days. It was verbally reported by the farm manager that all of the infected piglets had recovered from the infection.

Two other experiments were performed on different pig farms in Canada, using the same protocol, to treat *C. difficile* enteritis. Two veterinarians were on site to help. Subsequently, both veterinarians verbally reported that all infected piglets (5 in each farm) had recovered from *C. difficile* Enteritis following oral administration of IMM-001 antibodies.

EXAMPLE 9

Clinical Efficacy of IMM-001 Polyclonal Antibodies for Treatment of Patients with *C. difficile* Infection in Four Centers Following oral administration of IMM-001 antibodies at 20 g or 10 g per day for 10 days, the patients demonstrated significant improvement in clinical symptoms, cured the disease and stool samples tested negative for *C. difficile* and/or *C. difficile* toxin. The results are shown in Table 6 and FIG. 10.

Clinical efficacy of oral polyclonal antibody therapy with IMM-001 for treatment of recurrent *C. difficile* infections (CDI) in elderly patients treated at the Toronto East General Hospital in Canada (i) An 82-year-old male patient with recurrent *C. difficile* infection (CDI) who failed to respond to antibiotic therapy with meteronidazole and vancomycin was hospitalized with severe diarrhea and colitis. His stool sample tested positive for *C. difficile* toxins. His gastroenterologist treated him with 20 g of IMM-001 polyclonal antibody powder orally for 10 days. The patient was completely cured with no clinical symptoms and no recurrence of CDI. His post-treatment stool sample tested negative for *C. difficile* toxin 10 days and 3 weeks after antibody therapy.

(ii) A 75-year old female patient with recurrent CDI who failed to respond to treatment with vancomycin and florastor was admitted to the hospital with *C. difficile* colitis. Her stool sample tested positive for *C. difficile* toxin. Her gastroenterologist treated the patient with 20 g of IMM-001 polyclonal antibody powder orally for 10 days. The patient was completely cured with no clinical symptoms and she was discharged from the hospital following antibody therapy. Her post-treatment stool sample tested negative for *C. difficile* toxin.

EXAMPLE 10

Clinical Efficacy of Oral Polyclonal Antibody Therapy with IMM-001 for Treatment of Recurrent *C. difficile* Infections (CDI) in Patients Treated at the Las Vegas Gastroenterology Institute, Las Vegas, Nev., USA (i) A 68-year old female colon cancer patient came to the Institute suffering from recurrent *C. difficile* infection (CDI) with copious diarrhea and dehydration. She failed to respond to the standard antibiotic treatment with metronidazole and vancomycin. Her stool sample tested positive for *C. difficile* toxins. Her attending gastroenterologist treated her with 20 g of IMM-001 polyclonal antibody powder orally for 10 days. The patient was cured with no clinical symptoms. Her post-antibody treatment stool sample tested negative for *C. difficile* toxin one week and 12 weeks following antibody therapy.

(ii) A second female patient had an antibiotic-resistant *C. difficile* infection (CDI) together with radiation enteritis. Her stool sample tested positive twice for *C. difficile* toxins. As she failed to respond to standard antibiotic treatment with metronidazole and vamcomycin, her gastroenterologist decided to treat her with 20 g of IMM-001 polyclonal antibody powder orally for 10 days. The patient was cured and her clinical symptoms were significantly improved. Her post-treatment stool sample tested negative for *C. difficile* toxin 2 days and one week following antibody therapy.

EXAMPLE 11

Clinical Efficacy of Oral Polyclonal Antibody Therapy with IM-01 for Treatment of Recurrent *C. difficile* Infections (CDI) with Epidemic Strain of *C. difficile* NAP/B1/027 in a Younger Patient Treated at the California Pacific Medical Center, San Francisco, Calif. USA An 11-year old boy had suffered with chronic *C. difficile* infections with profuse diarrhea and abdominal cramp for more than 11 months and had failed to respond to antibiotic treatment. During this period he had multiple recurrences, generally within 2-4 weeks post-cessation of antibiotic treatment with metronidazole and vancomycin. He suffered from diarrhea (up to 8 to 12 unformed stools per day with mucus and urgency). He was diagnosed as having been infected with an epidemic strain of *C. difficile* NAP/B1/027. As he failed antibiotic treatment many times, his Pediatric gastroenterologist treated him with 10 g of IMM-001 polyclonal antibody powder orally for 10 days. The patient was cured with significantly improved clinical symptoms without any recurrence and his stool sample remained *C. difficile* negative.

EXAMPLE 12

Clinical Efficacy of Oral Polyclonal Antibody Therapy with 20 g of IMM-001 Per Day for 10 Days for Treatment of *C. difficile* Infections (CDI) at the Center for Digestive Diseases, Sydney, Australia The clinical efficacy of IMM-001 antibodies in patients treated with 20 g and 10 g dosage, described in Example 12 & 13, is shown in FIG. 10

(i) A 52-old male patient had a history of *C. difficile* infection and diarrhea. He was diagnosed with a *C. difficile* infection (CDI), and his stool sample tested positive for *C. difficile* in culture. As there was no knowledge about his previous antibiotic treatment, his gastroenterologist treated him with 20 g of IMM-001 polyclonal antibody powder orally for 10 days. The patient was cured with significant improvement in clinical symptoms and his post-treatment stool sample tested negative for *C. difficile*.

(ii) A 57-year-old female patient came to the Center for Digestive Diseases with symptoms of pain on her right upper quadrant, alternating diarrhea up to 5 stools per day, with occasional constipation associated with bloating, occasional gas, nausea and lethargy. Her stool sample tested positive for *C. difficilie* in culture. As she was not responding to treatment with salazopyrin and somac, her gastroenterologist treated her with 20 g of IMM-001 polyclonal antibody powder orally for 10 days. The patient was cured with significant improvement in clinical symptoms and her post-treatment stool sample tested negative for *C. difficile*.

(iii) A 53-old male patient with a history of IBS (Irritable Bowel Syndrome) for 15-20 years, came to the clinic with lower abdominal pain and discomfort in the right iliac fossa (RIF). He had attacks of diarrhea with some foods, nausea and marked gas production/flatulence with known diverticulosis. He was diagnosed with *C. difficile* infection (CDI) as his stool sample tested positive for *C. difficile* in culture. He was taking prednisone and salazopyrin. His gastroenterologist treated him with 20 g of IMM-001 polyclonal antibody powder orally for 10 days. The patient was cured with marked improvement in clinical symptoms and regained energy. His post-treatment stool sample tested negative for *C. difficile*.

(iv) A 57-year old male patient came to the clinic as he had diarrhea, abdominal pain and bloating. He was diagnosed by his gastroenterologist for *C. difficile* Infections (CDI). His stool sample tested positive for *C. difficile* in culture. As he failed two courses of treatment with metronidazole, his gastroenterologist treated him with 20 g of IMM-001 polyclonal antibody powder orally for 10 days. The patient was cured with significant improvement in clinical symptoms and his post-treatment stool samples were negative for *C. difficile*.

(v) A 52-old male patient had a history of *C. difficile* infection (CDI) and failed antibiotic therapy. He was again diagnosed with a *C. difficile* infections when his stool sample tested positive for *C. difficile* in culture. His Gastroenterologist treated him with 20 g of IMM-001 polyclonal antibody powder orally for 10 days. The patient was cured with significant improvement in clinical symptoms and his post-treatment stool samples tested negative for *C. difficile*.

(vi) A 43-year old female patient had a *C. difficile* infection with pseudomembranous colitis. Her stool sample tested positive for *C. difficile* in culture. Her gastroenterologist treated her with 20 g of IMM-001 polyclonal antibody powder orally for 10 days. The patient was cured with significant improvement in clinical symptoms and his post-treatment stool samples tested negative for *C. difficile*.

(vii) An 18-year old female patient came to the clinic with diarrhea. She was diagnosed with a *C. difficile* infection (CDI). Her stool sample tested positive for *C. difficile* toxins and *C. difficile* in culture. Her gastroenterologist treated her with 20 g of IMM-001 polyclonal antibody powder for 10 days. The patient was cured with marked improvement in clinical symptoms. Her post-treatment stool sample tested negative for *C. difficile* toxin and for *C. difficile*.

(viii) A 66-year old female patient (G-C) came to the clinic suffering from diarrhea with 5-6 stools per day, with occasional blood, urgency, but with no pain. Her stool sample was positive for *C. difficile* toxin and *C. difficile* in culture. Her gastroenterologist decided to treated her with 20 g of IMM-001 polyclonal antibody powder orally for 10 days. The patient was cured with significant improvement in clinical symptoms. Her post-antibody treatment stool sample tested negative for *C. difficile* toxin and *C. difficile* in culture.

(ix) A 49-year old female patient who had a history of Crohn's disease, came to the clinic with symptoms of rectal bleeding, diarrhea, with sub-umbilical pain but no hemorrhoids. Her stool sample tested positive for *C. difficile* toxin. As she failed to respond to treatment with maxalon, nexium, imuran, effexor, capinol, ciproxin and vancomycin, her gastroenterologist treated her with 20 g of IMM-001 polyclonal antibody powder orally for 10 days. The patient was cured with significant improvement in clinical symptoms and her post-antibody treatment stool sample tested negative for *C. difficile* toxin.

(x) A 41-year old female patient came to the clinic suffering from diarrhea with unformed porridgy type stools, 4-6 per day with no blood or mucus. Her stool sample tested positive for *C. difficile* in culture. As she failed to respond to antibiotic therapy with vancomycin 500 mg, her gastroenterologist treated her with 20 g of IMM-001 polyclonal antibody powder orally for 10 days. The patient was cured with marked improvement in clinical symptoms. Her post-antibody treatment stool sample tested negative for *C. difficile*.

(xi) A 66-year old female patient came to the clinic suffering from watery diarrhea with explosive stool 10 per day with mucus. She was diagnosed with a *C. difficile* infection (CDI). As she failed to respond to treatment with colazide, bismuth and vancomycin, her gastroenterologist treated her with 20 g of IMM-001 polyclonal antibody powder orally for 10 days. The patient was cured and became asymptomatic. Her post-treatment stool sample tested negative for *C. difficile* toxin and *C. difficile*.

(xii) A 60-year old female patient came to the clinic suffering from abdominal pain and diarrhea with watery stool 10 per day. Her stool sample tested positive for *C. difficile* toxin and *C. difficile* in culture. As she failed to respond to treatment with metronidazole and salofalk, her gastroenterologist treated her with 20 g of IMM-001 polyclonal antibody powder orally for 10 days. The patient was cured with marked improvement in clinical symptoms. Her post-antibody therapy stool sample tested negative for *C. difficile* toxin and *C. difficile*.

(xiii) A 42-year old female patient came to the clinic suffering from abdominal pain, bloating and soft stool 2 per day. Her stool sample tested positive for *C. difficile* toxin. As she failed to respond to antibiotic treatment with metronidazole and vancomycin, her gastroenterologist treated her with 20 g of IMM-001 polyclonal antibody powder orally for 10 days. The patient was cured with significant improvement in clinical symptoms. Her post-antibody therapy stool sample tested negative for *C. difficile* toxin.

(xiv) A 56-year-old female patient came to the clinic suffering from explosive diarrhea, liquid stool 1 per day, wind and abdominal pain. Her stool sample tested positive for *C. difficile* in culture. She was taking salofalk prior to her visit. Her Gastroenterologist treated her with 20 g of IMM-001 polyclonal antibody powder orally for 10 days. The patient was cured with marked improvement in clinical symptoms. Her post-antibody therapy stool sample tested negative for *C. difficile*.

(xv) A 67-year old female patient came to the center suffering from diarrhea with explosive watery stool 10-15 per day, abdominal pain and nausea. Her stool sample tested positive for *C. difficile* in culture. As she failed to respond to treatment with metronidazole, ciproxin, colazide and somac, her gastroenterologist decided to treat her with 20 g of IMM-001 polyclonal antibody powder orally for 10 days. The patient was cured with significant improvement in clinical symptoms and her post-antibody treatment stool sample tested negative for *C. difficile*.

(xvi) A 23-year old female patient came to the clinic suffering from gastric problems associated with soft stool daily, incomplete emptying, some gas and bloating. Her stool sample tested positive for *C. difficile* in culture. As she had been treated previously with vancomycin, mosapride and colgout, her gastroenterologist decided to treat her with 20 g of IMM-001 polyclonal antibody powder orally for 10 days. The patient was cured with significant improvement in clinical symptoms. Her post-antibody treatment stool sample tested negative for *C. difficile*.

(xvii) A 50-year old female patient came to the Center for Digestive Disease suffering from irregular bowel motions, and loose to hard stool 2 per day, gas, bloating, wheat and red wine intolerance, and uncontrollable diarrhea when stressed. Her stool sample tested positive for *C. difficile* in culture. Her gastroenterologist decided to treat her with 20 g of IMM-001 polyclonal antibody powder orally for 10 days. The patient was cured without any clinical symptoms and her post-treatment stool sample tested negative for *C. difficile*.

(xviii) A 38 year-old female patient came to the clinic suffering from diarrhea with soft stool 3-4 per day, abdominal cramping, headaches, nausea and joint pain. Her stool sample was tested positive for *C. difficile* toxin and *C. difficile* in culture. As her gastroenterologist did not have information regarding her previous treatment, he decided to treat with 20 g of IMM-001 polyclonal antibody powder orally for 10 days. The patient was cured with no clinical symptoms: no nausea, no cramps, no headaches and no joint pain, with normal stool. Her post-treatment stool sample tested negative for *C. difficile* and *C. difficile* toxins.

(xix) A 93-year old female patient came to the Center for Digestive Disease suffering from urgency, explosive watery diarrhea 2-3 times per week with no nausea or pain. She was diagnosed with a *C. difficile* infection. As she failed to respond to treatment with Salofalk and Imodium, her gastroenterologist treated her with 20 g of IMM-001 polyclonal antibody powder orally for 10 days. The patient was cured with significant improvement in clinical symptoms, 1-3 formed stools per day, no leakage or incontinence and improved appetite.

(xx) A 75-year old female patient came to the clinic with symptoms of watery diarrhea 5 per day, occasional incontinence with lower abdominal pain, and was suspected of having antibiotic-associated diarrhea due to her prior treatment with Augmentin for bladder infection. She was receiving treatment with Salofalk and Questran. Her stool sample tested positive for *C. difficile* in culture. Her gastroenterologist treated her with 20 g of IMM-001 polyclonal antibody powder orally for 10 days. The patient was cured with significant improvement in clinical symptoms: she had 1-2 semi-formed stools per day, no pain and felt well. Her post-antibody treatment stool sample tested negative for *C. difficile*.

(xxi) A 45-year old male patient came to the clinic suffering from soft stool 2 per day, food sensitivity and fatigue. His stool sample tested positive for *C. difficile* in culture. As he failed to respond to treatment with vancomycin, his gastroenterologist treated him with 20 g of IMM-001 polyclonal antibody powder orally for 10 days. The patient showed marked improvement in clinical symptoms and his post-treatment stool sample tested negative for *C. difficile*.

(xxii) A 70-year old female patient came to the Center for Digestive Disease suffering from abdominal pain and soft stool. Her stool sample tested positive for *C. difficile* in culture. As she failed to respond to treatment with antibiotics vancomycin and rifampicin, her gastroenterologist treated her with 20 g of IMM-001 polyclonal antibody powder orally for 10 days. The patient was cured with significant improvement in clinical symptoms. Her post-treatment stool sample tested negative for detection of *C. difficile*.

(xxiii) A 53-year-old female patient came to the Center for Digestive disease suffering from intermittent lower abdominal and intra-umbilical pain, no constipation or diarrhea and had had a previous *Klebsiella oxyloca*. She was diagnosed with *C. difficile* infection (CDI). Her gastroenterologist treated her with 20 g of IMM-001 polyclonal antibody powder orally for 10 days. The patient was cured without any clinical symptoms. Her post-treatment stool sample tested negative for *C. difficile*.

(xxiv) A 44-year-old female patient came to the Center for Digestive Disease suffering from clinical symptoms including explosive diarrhea, loose stool 8-10 per day, urgency, nausea and abdominal pain. She was diagnosed with a *C. difficile* infection (CDI). Prior to the visit, she has been treated with Salofalk, rifampicin and metronidazole. As she had failed to respond to treatment with the antibiotics, her gastroenterologist decided to treat her with 20 g of IMM-001 polyclonal antibody powder orally for 10 days. The patient was cured with marked improvement in clinical symptoms and her post-treatment stool sample tested negative for *C. difficile*.

EXAMPLE 13

Clinical Efficacy of Oral Polyclonal Antibody Therapy with 10 g/Day of IMM-001 for Treatment of *C. difficile* Infections (CDI) in the Center for Digestive Diseases, Sydney, Australia (i) A 33-year old female patient diagnosed previously with ulcerative colitis (UC) came to the center suffering from diarrhea with soft stool 5 per day, urgency, and gas. Her stool sample was tested positive for *C. difficile* in culture. As she was already taking salazopyrine and ciproxin, her gastroenterologist decided to treat her with 10 g of IMM-001 polyclonal antibody powder orally for 10 days. The patient was cured with marked improvement in clinical symptoms. Her post-treatment stool sample tested negative for *C. difficile*. As she was cured, her gastroenterologist stopped her medication for UC.

(ii) A 47-year old female patient came to the center suffering from epigastric pain, burping, lower abdominal pain and constipation. Her stool sample tested positive for *C. difficile* in culture. Her gastroenterologist decided to treat her with 10 g of IMM-001 polyclonal antibody powder orally for 10 days. The patient was cured with marked improvement in clinical symptoms. Her post-treatment stool sample tested negative for *C. difficile*.

(iii) A 42-year old female patient suffered from Crohn's disease, abdominal pain, semi-formed stools 2 per day and joint pain. Her stool sample tested positive for *C. difficile* in culture. Her gastroenterologist treated her with 10 g of IMM-001 polyclonal antibody powder orally for 10 days. The patient was cured with marked improvement in clinical symptoms. Her post-treatment stool sample tested negative for *C. difficile*.

(iv) A 38-year old female patient came to the center suffering from diarrhea with loose stool 4 per day, bleeding and abdominal pain. Her stool sample tested positive for *C. difficile* in culture. As she failed to respond to antibiotic treatment with metronidazole, her gastroenterologist treated her with 10 g of IMM-001 polyclonal antibody powder orally for 10 days. The patient was cured with significant improvement in clinical symptoms. Her post-treatment stool sample tested negative for *C. difficile*.

(v) A 73-year-old female patient ((I-K) who had a hemicolectomy, and was suffering from watery diarrhea up to 3 stools per day with abdominal cramps and urgency for 2-3 months came to the clinic. Her stool sample tested positive for *C. difficile* in culture. As she was taking colazide, her gastroenterologist treated her with 10 g of IMM-001 polyclonal antibody powder orally for 10 days. The patient was cured with marked improvement in clinical symptoms and no recurrence of CDI. Also, her post-treatment stool sample tested negative for *C. difficile*.

(vi) A 33-year-old female patient came to the center suffering from diarrhea and flatulence but without abdominal pain. Her stool sample tested positive for both *C. difficile* toxin and *C. difficile* in culture. As she was taking salazopyrin, her gastroenterologist treated her with 10 g of IMM-001 polyclonal antibody powder orally for 10 days. The patient was cured with significant improvement in clinical symptoms. Her post-treatment stool sample tested negative for both *C. difficile* and *C. difficile* toxin.

(vii) A 66-year-old female patient came to the Center for Digestive Diseases suffering from upper abdominal discomfort, right upper quadrant burning, and heaviness in lower abdomen. Her stool sample tested positive for *C. difficile* toxin and *C. difficile* in culture. As she failed to respond to antibiotic treatment with doxycycline and metronidazole, her gastroenterologist treated her with 10 g of IMM-001 polyclonal antibody powder orally for 10 days. The patient was cured with marked improvement in clinical symptoms. Her post-treatment stool sample tested negative for both *C. difficile* and *C. difficile* toxin.

(viii) A 59-year-old female patient came to the center suffering from lower abdominal pain, alternating diarrhea and constipation, as well as having had gastroenteritis for the last 6-months. Her stool sample was tested positive for *C. difficile* in culture and *C. difficile* toxins. Her gastroenterologist treated her with 10 g of IMM-001 polyclonal antibody powder orally for 10 days. The patient showed marked improvement in clinical symptoms. Her post-treatment stool sample tested negative for both *C. difficile* in culture and *C. difficile* toxin.

(ix) A 69-year-old female patient came to the Center for Digestive Diseases suffering from episodic and recurrent diarrhea with up to 12 stools per day, lower abdominal cramps, occasional bloating and gas. Her stool sample tested positive for *C. difficile* in culture. Her gastroenterologist treated her with 10 g of IMM-001 polyclonal antibody powder orally for 10 days. The patient showed marked improvement in clinical symptoms.

The scope of the claims should not be limited by the preferred embodiments set forth in the examples but should be given the broadest interpretation consistent with the description as a whole.

TABLE: 1

Reactivity of IMM-001 polyclonal antibodies to C. *difficile* toxins produced by genetically diverse C. *difficile* strains

| Diverse C. *difficile* strains | Ribotypes | Toxinotypes | TcdC | Binary Toxin | Control IgY Reactivity with C. *difficile* Toxins by ELISA (OD$_{405}$) | IMM-001 reactivity with C. *difficile* Toxins by ELISA (A405 nm) |
|---|---|---|---|---|---|---|
| 2-14 | 004 | 21 | wt | positive | 0.3 | 1.56 |
| 3-31 | 002 | 0 | wt | negative | 0.15 | 1.40 |
| 3-32 | 002 | 6 | 30 bp | positive | 0.25 | 1.32 |
| 3-39 | 019 | 9 | wt | positive | 0.29 | 1.29 |
| 4-12 | 003 | 8 | wt | negative | 0.28 | 1.27 |
| 5-31 | NAP/81/027 | 3 | del | positive | 0.38 | 1.47 |
| 6-15 | 002 | 2 | wt | negative | 0.31 | 1.40 |
| 6-30 | NAP/81/027 | 3 | del | positive | 0.37 | 1.20 |
| 10-7 | NAP/81/027 | 3 | del | positive | 0.34 | 0.92 |
| 92146 | 002 | 0 | wt | negative | 0.29 | 1.1 |
| VPI-10463 | 003 | 0 | wt | negative | 0.31 | 1.8 |

TABLE 2

Reactivity of IMM-001 polyclonal antibodies to C. *difficile* spores produced by genetically diverse C. *difficile* strains

| Diverse C. *difficile* strains | Ribotypes | Toxino-types | Control IgY Reactivity with C. *difficile* spores by ELISA (A405 nm) | IMM-001 reactivity with C. *difficile* spores by ELISA (A405 nm) |
|---|---|---|---|---|
| 2-14 | 004 | 21 | 0.31 | 1.25 |
| 3-31 | 002 | 0 | 0.18 | 1.42 |
| 3-32 | 002 | 6 | 0.20 | 0.78 |
| 3-39 | 019 | 9 | 0.30 | 1.15 |
| 4-12 | 003 | 8 | 0.31 | 1.20 |
| 5-31 | NAP/B1/027 | 3 | 0.35 | 0.87 |
| 6-15 | 002 | 2 | 0.31 | 1.04 |
| 6-30 | NAP/B1/027 | 3 | 0.33 | 0.98 |
| 10-7 | NAP/B1/027 | 3 | 0.34 | 2.23 |
| 92146 | 002 | 0 | 0.28 | 1.22 |

TABLE 3

Reactivity of IMM-001 polyclonal antibodies to C. *difficile* bacteria of diverse genetic origin

| Diverse C. *difficile* strains | Toxinotypes | Ribotypes | IMM-001 Reactivity with C. *difficile* by ELISA (A 405 nm) |
|---|---|---|---|
| 5-31 | 3 | NAP1/B1/027 | 0.92 |
| 6-30 | 3 | NAP1/B1/027 | 0.95 |
| 10-7 | 3 | NAP1/B1/027 | 0.88 |
| 92146 | 0 | 002 | 0.80 |
| VPI 10463 | 0 | 003 | 0.72 |

TABLE 4

Toxin Neutralization ability of IMM-001 antibodies to toxins produced by genetically diverse C. *difficile* strains

| Diverse C. *difficile* strains tested | Ribotypes | Toxinotypes | 100% Neutralizing Efficacy of IMM-001 (antibody concentration μg/mL) to toxins generated from C. *difficile* strains with diverse Ribotypes |
|---|---|---|---|
| 3-32 | 002 | 6 | 100 |
| 3-39 | 019 | 9 | 50 |
| 5-31 | NAP/B1/027 | 3 | 300 |
| 6-30 | NAP/B1/027 | 3 | 0.7 |
| 10-7 | NAP/B1/027 | 3 | 60 |
| 92146 | 002 | 0 | 60 |
| VPI 10463 | 003 | 0 | 20 |

TABLE 5

Effect of IMM-001 polyclonal antibodies on inhibition of C. *difficile* adhesion onto Caco-2 cells

| Incubation at concentration(s) | Average number of adherent bacteria detected C. *difficile* per microscopic field | | Percent adherence inhibition compared with control IgY |
|---|---|---|---|
| | Control IgY | IM-01 antibodies | |
| 1.0 mg/mL | 29.7 | 14.9 | 42% |
| 0.5 mg/mL | 42.1 | 16.1 | 55% |
| 0.25 mg/ml | 54.1 | 13.9 | 73% |

TABLE 6

Clinical Efficacy of Oral Polyclonal Antibody Therapy in Patients with Clostridium difficile infections (CDI) in Proof-of-Concept clinical Studies

| Study Centers & Gastroenterologists collaborated | Clinical symptoms & Diagnostic tests: prior to antibody therapy | | Number of patients with CDI received antibody therapy | Clinical symptoms & Diagnostic tests: -post -treatment | | Comments |
|---|---|---|---|---|---|---|
| | Symptoms | Diagnostic tests Toxins Culture | | Symptoms | Diagnostic tests Toxins Culture | |
| Gastroenterology Institute, Las | Copious diarrhea | +ve −ve | 2 | Significantly improved | −ve −ve | Cured 2/2 patients |

| Location | Symptoms | | Number | Clinical outcome | | Result |
|---|---|---|---|---|---|---|
| Vegas, NV. USA | with dehydration, relapse cases of CDI | | | | | treated. Effective treatment with no side effects |
| Toronto East General Hospital, Toronto, ON. Canada | Diarrhea, abdominal pain, discomfort, relapse cases of CDI | +ve Not done | 3 | Clinical symptoms significantly improved in 2 patients and partially improved in one patient. | −ve Not done | Cured 2/3 patients. |
| California Pacific Medical Center, San Francisco, USA | Diarrhea, abdominal pain, discomfort, relapse cases of CDI, | +Ve Not done | 1 | Clinical symptoms significantly improved | −ve Not done | Cured 1/1 patient |
| Center for Digestive Diseases, Sydney, Australia | Diarrhea, abdominal pain, discomfort, relapse CDI | +Ve −ve | 17 | Clinical symptoms significantly improved in all patients except one | −ve −ve (16/17) +ve +ve (1/17) | Cured 16/17 patients |
| Center for Digestive Diseases, Sydney, Australia | Diarrhea, abdominal pain, discomfort, relapse CDI | +ve/−ve +ve | 80 | Clinical symptoms significantly improved in all patients except two | −ve −ve (77/80) −ve +ve (3/80) | Cured 78/80 patients |

A total of 103 patients with CDI received oral antibody therapy and 99 patients were cured with significant clinical improvement with no relapse.

REFERENCES

1. Paresdes-Sabja, D and Sarker, M. R. J Med. Microbial. 61: 1208, 2012
2. IMS Health incorporated information service: CDM Hospital database for full year 2012.
3. US Department of Health & Human Services. Agency for Health Care Research and Quality, Jan. 25, 2012.
4. Miller B. A. et al. Infect Control Hosp Epidemiol. 32:387, 2011.
5. (APIC) National Prevalence study for *Clostridium difficile* in US Healthcare Facilities. Nov. 11, 2008.
6. Agency for healthcare research and Quality. Statistical Brief #124. *Clostridium difficile* infections (CDI) in hospital stays, January 2012.
7. Bouza, E. Clin. Microbial Infect. 18 (suppl.6): 5, 2012
8. Khanna, S. and pardi D. S. Mayo Clin Proc. 87: 1106, 2012.
9. Johnson, S. et al. Antimicrobial Agents & Chemotherapy 56: 4043, 2012
10. Ananthakrishnan A. N. Gastroenterol Hepatol. 8: 17, 2011
11. Sanchez-K. et al. J. Med. Microbial. 57:717, 2008.
12. Lowy, I. et al. N Engl. J Med. 362:197, 2010.
13. Basseri, R. J. et al. Gastroenterol. Hepatol. 7: 455, 2011
14. Hulisz, D. J. Manag Care Pharm 10: 299, 2004
15. Furnari, M. et al. J Gastrointestin Liver Dis. 21: 157, 2012.

The invention claimed is:

1. A method for treating a *Clostridium difficile* (*C. difficile*) infection comprising administering to an individual an effective amount of a polyclonal antibody composition,
   wherein said individual is selected from the group consisting of: an individual suffering from a *C. difficile* infection; an individual infected with *C. difficile*; an individual having a symptom of *C. difficile* associated disease; an individual having a predisposition towards *C. difficile* infection; an individual who is at risk of *C. difficile* infection; and an individual in a long term care facility; and
   wherein said polyclonal antibody composition is prepared by:
   a) immunizing a first group of egg-laying hens with an antigen prepared from *Clostridium difficile* Toxin A;
   b) immunizing a second group of egg-laying hens with an antigen prepared from *Clostridium difficile* Toxin B;
   c) immunizing a third group of egg-laying hens with an antigen prepared from *Clostridium difficile* spores;
   d) collecting eggs laid by said first group, said second group and said third group; and
   e) recovering polyclonal antibodies from said collected eggs.

2. The method according to claim 1, wherein the antigens are administered to the hens in combination with an adjuvant.

3. The method according to claim 2 wherein the adjuvant is MONTANIDE-ISA-70™ (mineral oil based adjuvant).

4. The method according to claim 1 wherein the polyclonal antibodies are recovered from the collected eggs by freeze-drying.

5. The method according to claim 1 wherein the polyclonal antibodies are recovered from the collected eggs by spray-drying.

6. The method according to claim 1 wherein the polyclonal antibody composition has a reciprocal antibody titer of <128,000.

7. The method according to claim 1 wherein the individual is infected with a *Clostridium difficile* strain that is a hypervirulent and/or antibiotic resistant *Clostridium difficile* strain.

8. The method according to claim 7 wherein the *Clostridium difficile* strain is selected from the group consisting of NAP/B1/027, CCL678, HMC553, Pitt45, CD196, montreal 5, montreal 7.1, MH5, Pitt2, CCL14137, UVA17, UVA30/TL42, and Pitt7.

9. The method according to claim 1 wherein the polyclonal antibody composition is administered until severity of symptoms of the *Clostridium difficile* infection has been reduced.

10. The method according to claim 1 wherein the effective amount is between about 2-40 g.

11. The method according to claim 1 wherein the effective amount is between about 5-30 g.

12. The method according to claim 1 wherein the effective amount is between about 5-20 g.

13. The method according to claim 1 wherein the polyclonal antibody composition is administered daily for a period of at least 7 days.

14. The method according to claim 1 wherein the polyclonal antibody composition is administered daily for a period of at least 10 days.

15. The method according to claim 1 wherein the polyclonal antibody composition is administered daily for a period of about 7-21 days.

16. The method according to claim 1 wherein the polyclonal antibody composition is administered daily for a period of about 10-14 days.

17. The method according to claim 1 wherein the polyclonal antibodies are purified from the collected eggs.

18. The method according to claim 1 wherein the polyclonal antibody composition is administered orally.

* * * * *